(12) United States Patent
Iwase et al.

(10) Patent No.: US 10,872,237 B2
(45) Date of Patent: Dec. 22, 2020

(54) IMAGE PROCESSING SYSTEM, PROCESSING METHOD, AND STORAGE MEDIUM

(71) Applicant: CANON KABUSHIKI KAISHA, Tokyo (JP)

(72) Inventors: Yoshihiko Iwase, Kyoto (JP); Hiroyuki Shinbata, Tama (JP); Makoto Sato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/658,590

(22) Filed: Oct. 21, 2019

(65) Prior Publication Data

US 2020/0050852 A1 Feb. 13, 2020

Related U.S. Application Data

(63) Continuation of application No. 15/789,226, filed on Oct. 20, 2017, now Pat. No. 10,482,326, which is a continuation of application No. 15/044,429, filed on Feb. 16, 2016, now Pat. No. 9,824,273, which is a (Continued)

(30) Foreign Application Priority Data

Jan. 27, 2012 (JP) .................. 2012-015935

(51) Int. Cl.
*G06T 7/64* (2017.01)
*G06K 9/00* (2006.01)
*A61B 3/00* (2006.01)
*G06T 7/00* (2017.01)

(52) U.S. Cl.
CPC ........ *G06K 9/00617* (2013.01); *A61B 3/0025* (2013.01); *G06T 7/0012* (2013.01); *G06T 7/64* (2017.01); *G06T 2207/10101* (2013.01); *G06T 2207/30041* (2013.01)

(58) Field of Classification Search
CPC combination set(s) only.
See application file for complete search history.

(56) References Cited

U.S. PATENT DOCUMENTS

| 3,380,334 A | 4/1968 | Fischer |
| 5,321,501 A | 6/1994 | Swanson et al. |
| 6,293,674 B1 | 9/2001 | Huang et al. |

(Continued)

FOREIGN PATENT DOCUMENTS

| JP | H09164141 A | 6/1997 |
| JP | H09236407 A | 9/1997 |

(Continued)

OTHER PUBLICATIONS

Japanese office action issued in corresponding application No. JP 2012015935 dated Jan. 5, 2016.

(Continued)

*Primary Examiner* — Tsung Yin Tsai
(74) *Attorney, Agent, or Firm* — Carter, DeLuca & Farrell LLP

(57) ABSTRACT

An image processing system includes: an analysis unit configured to obtain information indicating a degree of curvature of a retina from a tomographic image of an eye to be examined; and an obtaining unit configured to obtain a category of the eye to be examined based on an analysis result.

12 Claims, 23 Drawing Sheets

Related U.S. Application Data continuation of application No. 13/748,766, filed on Jan. 24, 2013, now abandoned.

(56) References Cited

U.S. PATENT DOCUMENTS

| | | | |
|---|---|---|---|
| 6,325,512 B1 | 12/2001 | Wei | |
| 6,356,036 B1 | 3/2002 | Zhou | |
| 6,735,331 B1 | 5/2004 | Binnun et al. | |
| 7,146,983 B1 | 12/2006 | Hohla et al. | |
| 7,347,548 B2 | 3/2008 | Huang et al. | |
| 7,384,146 B2* | 6/2008 | Covannon | A61F 9/008 |
| | | | 351/206 |
| 7,497,574 B2 | 3/2009 | Watanabe et al. | |
| 8,081,808 B2 | 12/2011 | Huang et al. | |
| 8,761,481 B2 | 6/2014 | Nakano et al. | |
| 8,870,377 B2 | 10/2014 | Iwase et al. | |
| 9,042,622 B2* | 5/2015 | Uchida | A61B 3/102 |
| | | | 382/131 |
| 9,053,536 B2 | 6/2015 | Imamura et al. | |
| 9,149,183 B2 | 10/2015 | Iwase et al. | |
| 9,265,418 B2 | 2/2016 | Iwase | |
| 9,279,660 B2 | 3/2016 | Sato et al. | |
| 9,436,994 B2 | 9/2016 | Furukawa et al. | |
| 9,824,273 B2* | 11/2017 | Iwase | G06T 7/0012 |
| 10,297,352 B2 | 5/2019 | Sakagawa et al. | |
| 10,674,909 B2* | 6/2020 | Kano | G06T 3/0068 |
| 2004/0008877 A1* | 1/2004 | Leppard | G01M 11/0214 |
| | | | 382/141 |
| 2005/0018133 A1 | 1/2005 | Huang et al. | |
| 2007/0103693 A1 | 5/2007 | Everett et al. | |
| 2007/0159601 A1 | 7/2007 | Ho et al. | |
| 2007/0195269 A1 | 8/2007 | Wei et al. | |
| 2007/0216909 A1 | 9/2007 | Everett et al. | |
| 2007/0291277 A1* | 12/2007 | Everett | G01N 21/4795 |
| | | | 356/497 |
| 2009/0033868 A1 | 2/2009 | Huang et al. | |
| 2009/0123036 A1 | 5/2009 | Huang et al. | |
| 2009/0123044 A1 | 5/2009 | Huang et al. | |
| 2009/0268159 A1 | 10/2009 | Xu et al. | |
| 2009/0268161 A1 | 10/2009 | Hart et al. | |
| 2009/0323023 A1 | 12/2009 | Kogawa et al. | |
| 2010/0111373 A1 | 5/2010 | Chin et al. | |
| 2010/0220914 A1 | 9/2010 | Iwase et al. | |
| 2010/0290004 A1 | 11/2010 | Huang et al. | |
| 2010/0290005 A1 | 11/2010 | Huang et al. | |
| 2011/0137157 A1 | 6/2011 | Imamura et al. | |
| 2011/0299034 A1* | 12/2011 | Walsh | A61B 3/0091 |
| | | | 351/206 |
| 2012/0051611 A1* | 3/2012 | Takama | G06T 7/12 |
| | | | 382/128 |
| 2012/0057127 A1 | 3/2012 | Iwase et al. | |
| 2012/0113390 A1* | 5/2012 | Torii | A61B 3/12 |
| | | | 351/208 |
| 2012/0120368 A1* | 5/2012 | Fujimora | A61B 3/12 |
| | | | 351/206 |
| 2012/0140179 A1 | 6/2012 | Miyasa et al. | |
| 2012/0148130 A1 | 6/2012 | Nakano et al. | |
| 2012/0249769 A1* | 10/2012 | Naba | A61B 3/12 |
| | | | 348/78 |
| 2012/0274898 A1 | 11/2012 | Sadda et al. | |
| 2013/0136326 A1 | 5/2013 | Iwase et al. | |
| 2013/0194546 A1* | 8/2013 | Iwase | G06T 7/0012 |
| | | | 351/206 |
| 2016/0097632 A1 | 4/2016 | Sumiya et al. | |
| 2017/0112377 A1* | 4/2017 | Shiba | G06T 7/11 |
| 2017/0372132 A1 | 12/2017 | Iwase et al. | |
| 2018/0253812 A1 | 9/2018 | Iwase et al. | |

FOREIGN PATENT DOCUMENTS

| | | |
|---|---|---|
| JP | 2007319416 A | 12/2007 |
| JP | 2008061848 A | 3/2008 |
| JP | 2008073099 A | 4/2008 |
| JP | 2008089566 A | 4/2008 |
| JP | 2010094381 A | 4/2010 |
| JP | 2010200920 A | 9/2010 |
| JP | 2010279439 A | 12/2010 |
| JP | 2011030626 A | 2/2011 |
| JP | 2011092702 A | 5/2011 |
| JP | 2011515194 A | 5/2011 |
| JP | 2011224264 A | 11/2011 |

OTHER PUBLICATIONS

Medical examination data health management system VisualHealth. CheckUp simple health guidance edition; URL: https://web.archive.org/web/20100102011843/http://www.gikosha.co.jp/SMIS/SMIS_CON/VHN_04.html), Jan. 2, 2010.

VisualHealth.Navi Personal 1.01; (URL: http://www.vector.co.jp/soft/dl/winnt/home/se478747.html) Oct. 16, 2007.

VisualHealth.Navi personal; URL: https://web.archive.org/web/20091227225217/ http://www.gikosha.co.jp/SMIS/SMIS_CON/VHN_01.html, Dec. 27, 2009.

"Example of the analysis charts of personal medical checkup data"; URL: http://www.gikosha.co.jp/SMIS/SMIS_CON/SMIS_CHRT011.html.

"Cooperation between the chart"; URL: http://www.gikosha.co.jp/SMIS/SMIS_CON/SMIS_CHRT021.html.

Japanese office acion issued in corresponding application No. 2012015935 dated Aug. 1, 2016.

"Example of the analysis charts of assemblage medical checkup data"; URL: http://www.gikosha.co.jp/SMIS/SMIS_CON/SMIS_CHRT012_html.

Japanese Office Action dated Sep. 14, 2018 in corresponding Japanese Patent Application No. 2017-196377, with English translation.

Notice of Reasons for Refusal issued by the Japan Patent Office dated Jun. 15, 2020 in corresponding JP Patent Application No. 2019-085755, with English translation.

Japanese Office Action dated Nov. 6, 2020, for Corresponding Japanese Application No. 2019-085755.

\* cited by examiner

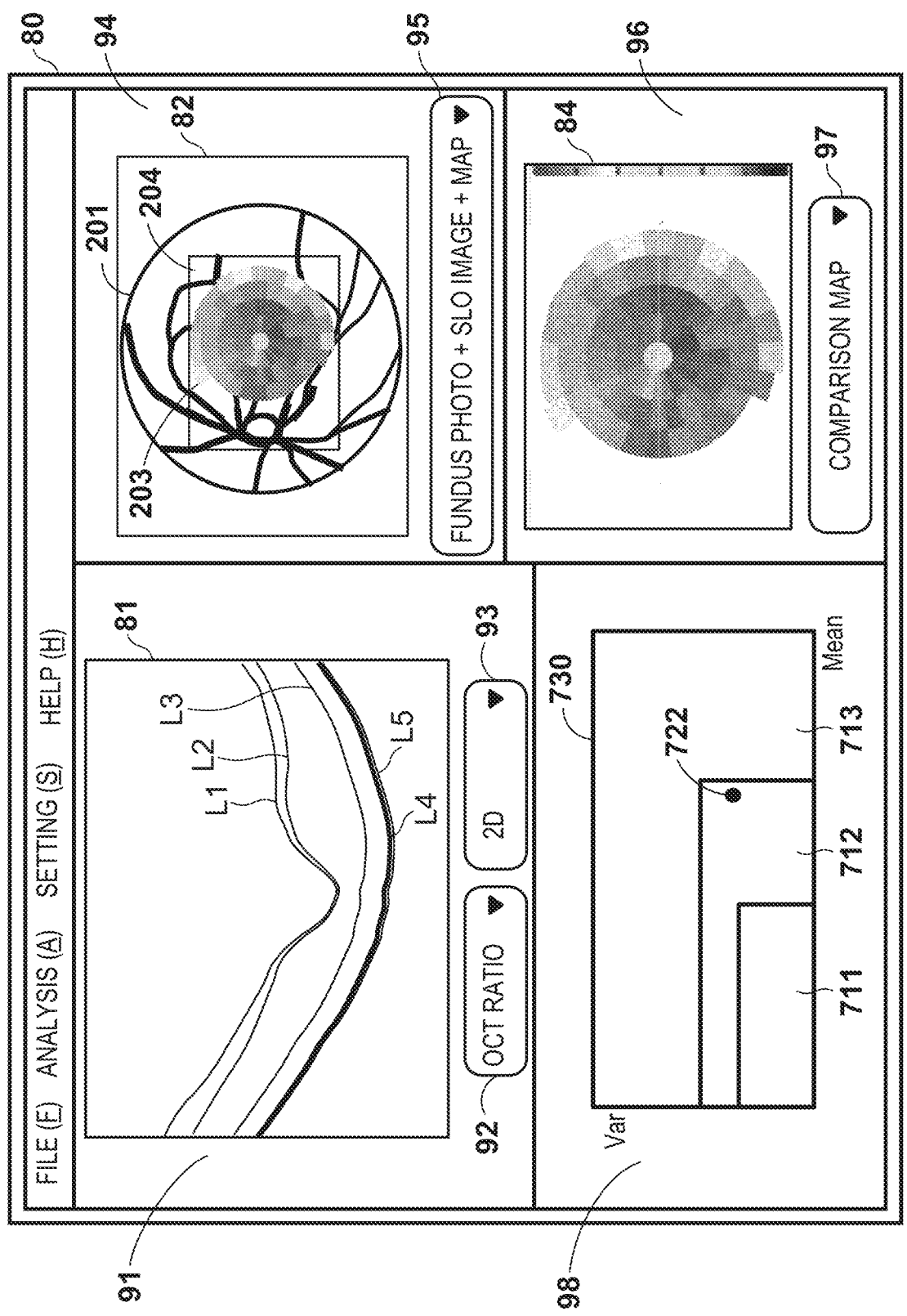

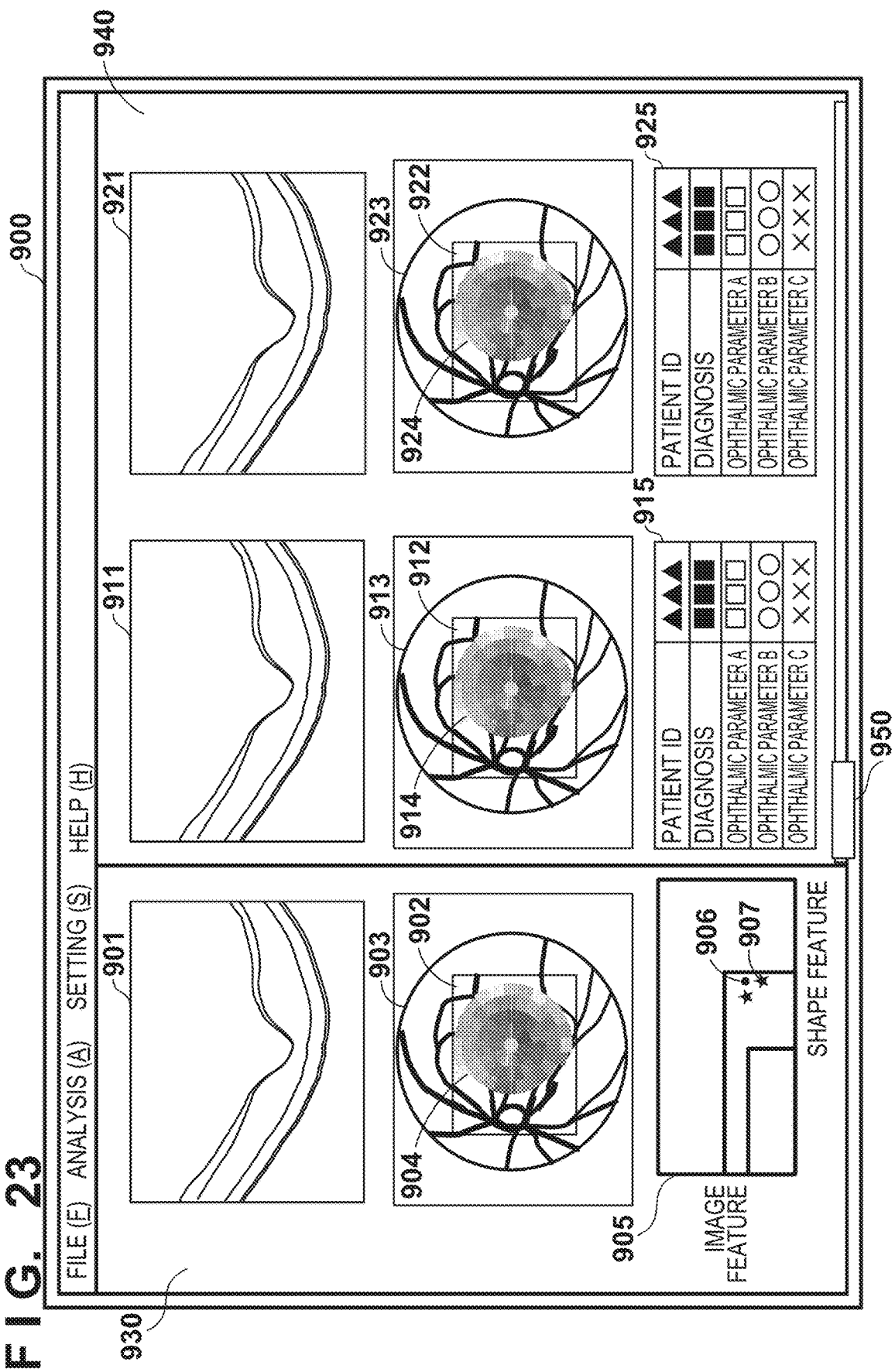

IMAGE PROCESSING SYSTEM, PROCESSING METHOD, AND STORAGE MEDIUM

CROSS REFERENCE TO RELATED APPLICATIONS

This application is a continuation of U.S. patent application Ser. No. 15/789,226, filed on Oct. 20, 2017, which is a continuation of U.S. patent application Ser. No. 15/044,429, filed on Feb. 16, 2016, now U.S. Pat. No. 9,824,273, which is a continuation of U.S. patent application Ser. No. 13/748,766, filed on Jan. 24, 2013, which claims the benefit of and priority to Japanese Patent Application No. 2012-015935, filed on Jan. 27, 2012, the entire contents of each of which are hereby incorporated by reference herein in their entireties.

BACKGROUND OF THE INVENTION

Field of the Invention

The present invention relates to an image processing system, processing method, and storage medium.

Description of the Related Art

A tomography apparatus using an OCT (Optical Coherence Tomography), which utilizes interference caused by low coherent light, is known. By capturing an image of a fundus by such tomography apparatus, the state of interior of retinal layers can be three-dimensionally observed.

Imaging by the tomography apparatus is receiving a lot of attention since it is a technique helpful to give more adequate diagnoses of diseases. As a mode of such OCT, for example, a TD-OCT (Time Domain OCT) as a combination of a broadband light source and Michelson interferometer is known. The TD-OCT measures interfering light with back-scattered light of a signal arm by scanning a delay of a reference arm, thus obtaining depth resolution information.

However, it is difficult for the TD-OCT to obtain an image fast. For this reason, as a method of obtaining an image faster, an SD-OCT (Spectral Domain OCT) which obtains an interferogram by a spectroscope using a broadband light source is known. Also, an SS-OCT (Swept Source OCT) which measures spectral interference by a single-channel photodetector using a fast wavelength swept light source is known.

In this case, if a shape change of a retina can be measured in a tomographic image captured by each of these OCTs, a degree of progress of a disease such as glaucoma and a degree of recovery after treatment can be quantitatively diagnosed. In association with such technique, Japanese Patent Laid-Open No. 2008-073099 discloses a technique for detecting boundaries of respective layers of a retina from a tomographic image and measuring thicknesses of the layers based on the detection result using a computer, so as to quantitatively measure the shape change of the retina.

With the technique of Japanese Patent Laid-Open No. 2008-073099 described above, a tomographic image within a range designated on a two-dimensional image is obtained, and layer boundaries are detected to calculate layer thicknesses. However, three-dimensional shape analysis of retinal layers is not applied, and the shape analysis result is not effectively displayed.

SUMMARY OF THE INVENTION

The present invention has been made in consideration of the aforementioned problems, and provides a technique which allows to display a shape feature amount of an eye to be examined as a diagnosis target together with an index used as a criterion as to whether or not the eye to be examined suffers a disease.

According to one aspect of the present invention, there is provided an image processing system comprising: an analysis unit configured to obtain information indicating a degree of curvature of a retina from a tomographic image of an eye to be examined; and an obtaining unit configured to obtain a category of the eye to be examined based on an analysis result.

According to the present invention, a shape feature amount of an eye to be examined can be displayed together with an index used as a criterion as to whether or not the eye to be examined suffers a disease.

Further features of the present invention will become apparent from the following description of exemplary embodiments (with reference to the attached drawings).

BRIEF DESCRIPTION OF THE DRAWINGS

FIG. 21 is a view showing an example of the tomographic image observation screen 80;

FIG. 23 is a view showing an example of a tomographic image observation screen 900.

DESCRIPTION OF THE EMBODIMENTS

Embodiments according to the present invention will be described in detail hereinafter with reference to the accompanying drawings.

First Embodiment

Figure 1:
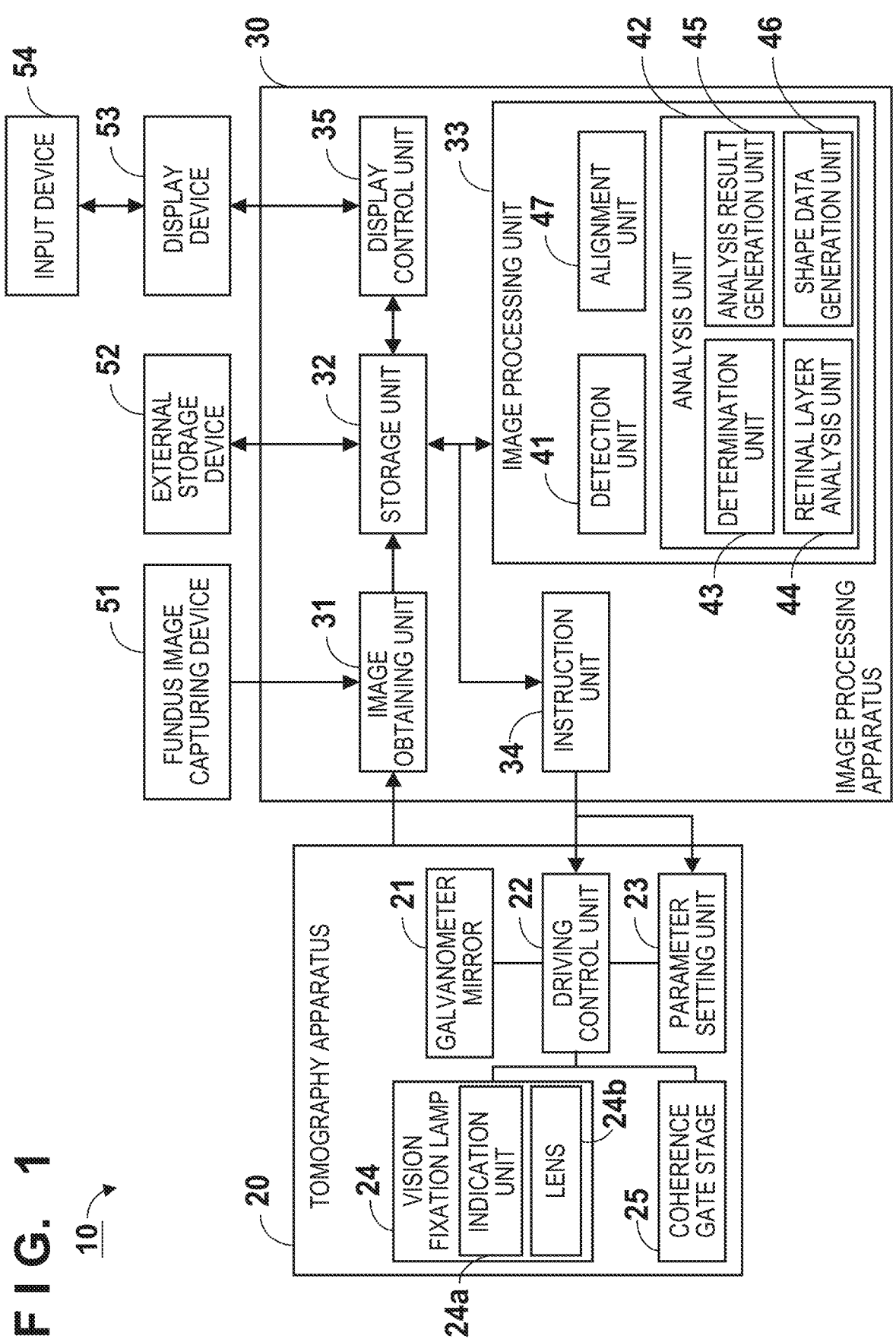
FIG. 1 is a block diagram showing an example of the arrangement of an image processing system 10 according to one embodiment of the present invention.

FIG. 1 is a block diagram showing an example of the arrangement of an image processing system 10 according to an embodiment of the present invention.

The image processing system 10 includes an image processing apparatus 30, tomography apparatus 20, fundus image capturing device 51, external storage device 52, display device 53, and input device 54.

The tomography apparatus 20 is implemented by, for example, an SD-OCT or SS-OCT, and captures a tomography image indicating a three-dimensional shape of a fundus using an OCT using interference caused by low coherent light. The tomography apparatus 20 includes a galvanometer mirror 21, driving control unit 22, parameter setting unit 23, vision fixation lamp 24, and coherence gate stage 25.

The galvanometer mirror 21 has a function of two-dimensionally scanning measurement light (irradiation light) on a fundus, and defines an imaging range of a fundus by the tomography apparatus 20. The galvanometer mirror 21 includes, for example, two mirrors, that is, X- and Y-scan mirrors, and scans measurement light on a plane orthogonal to an optical axis with respect to a fundus of an eye to be examined.

The driving control unit 22 controls a driving (scanning) range and speed of the galvanometer mirror 21. Thus, an imaging range in a planar direction (a direction orthogonal to an optical axis direction of measurement light) and the number of scan lines (scanning speed in the planar direction) on a fundus are defined.

The parameter setting unit 23 sets various parameters used in driving control of the galvanometer mirror 21 by the driving control unit 22. These parameters decide imaging conditions of a tomographic image by the tomography apparatus 20. For example, scan positions of scan lines, the number of scan lines, the number of images to be captured, and the like are decided. In addition, a position of the vision fixation lamp, scanning range, and scanning pattern, coherence gate position, and the like are also set. Note that the parameters are set based on an instruction from the image processing apparatus 30.

The vision fixation lamp 24 suppresses movement of a viewpoint by placing a bright spot in a visual field so as to prevent an eyeball motion during imaging of a tomographic image. The vision fixation lamp 24 includes an indication unit 24a and lens 24b. The indication unit 24a is realized by disposing a plurality of light-emitting diodes (LDs) in a matrix. Lighting positions of the light-emitting diodes are changed in correspondence with a portion as an imaging target under the control of the driving control unit 22. Light from the indication unit 24a is guided to the eye to be examined through the lens 24b. Light emerging from the indication unit 24a has a wavelength of, for example, 520 nm, and a desired pattern is indicated (lighted) under the control of the driving control unit 22.

The coherence gate stage 25 is arranged to cope with, for example, a different ophthalmic axis length of an eye to be examined. More specifically, an optical path length of reference light (to be interfered with measurement light) is controlled to adjust an imaging position along a depth direction (optical axis direction) of a fundus. Thus, optical path lengths of reference light and measurement light can be matched even for an eye to be examined having a different ophthalmic axis length. Note that the coherence gate stage 25 is controlled by the driving control unit 22.

In this case, a coherence gate indicates a position where optical distances of measurement light and reference light are equal to each other in the tomography apparatus 20. By controlling the coherence gate position, imaging on the side of retinal layers or that of an EDI (Enhanced Depth Imaging) method on the side deeper than the retinal layers is switched. When imaging is done using the EDI method, the coherence gate position is set on the side deeper than the retinal layers. Hence, when an image of the retinal layers is captured beyond an upper portion side of a tomographic image, the retinal layers can be prevented from appearing in the tomographic image while being folded back.

The fundus image capturing device 51 is implemented by, for example, a fundus camera, SLO (Scanning Laser Ophthalmoscope), or the like, and captures a (two-dimensional) fundus image of a fundus.

The external storage device 52 is implemented by, for example, an HDD (Hard Disk Drive) or the like, and stores various data. The external storage device 52 holds captured image data, imaging parameters, image analysis parameters, and parameters set by an operator in association with information (a patient name, age, gender, etc.) related to an eye to be examined.

The input device 54 is implemented by, for example, a mouse, keyboard, touch operation screen, and the like, and allows an operator to input various instructions. For example, the operator inputs various instructions, settings, and the like for the image processing apparatus 30, tomography apparatus 20, and fundus image capturing device 51 via the input device 54. The display device 53 is implemented by, for example, a liquid crystal display or the like, and displays (presents) various kinds of information for the operator.

The image processing apparatus 30 is implemented by, for example, a personal computer or the like, and processes various images. That is, the image processing apparatus 30 incorporates a computer. The computer includes a main control unit such as a CPU (Central Processing Unit), storage units such as a ROM (Read Only Memory) and RAM (Random Access Memory), and the like.

In this embodiment, the image processing apparatus 30 includes, as its functional units, an image obtaining unit 31, storage unit 32, image processing unit 33, instruction unit 34, and display control unit 35. Note that the units other than the storage unit 32 are implemented, for example, when the CPU reads out and executes a program stored in the ROM or the like.

The image processing unit 33 includes a detection unit 41, determination unit 43, retinal layer analysis unit 44, and alignment unit 47.

The image obtaining unit 31 obtains a tomographic image captured by the tomography apparatus 20 and a fundus image captured by the fundus image capturing device 51, and stores these images in the storage unit 32. Note that the storage unit 32 is implemented by, for example, the ROM, RAM, and the like.

The detection unit 41 detects retinal layers from the tomographic image stored in the storage unit 32.

The retinal layer analysis unit 44 analyzes the retinal layers to be analyzed. The retinal layer analysis unit 44 includes an analysis unit 42, analysis result generation unit 45, and shape data generation unit 46.

The determination unit 43 determines whether or not three-dimensional shape analysis processing of retinal layers is to be executed according to an imaging mode (a myopia analysis imaging mode and non-myopia analysis imaging mode). Note that the three-dimensional shape analysis indicates processing for generating three-dimensional shape data, and executing shape analysis of retinal layers using the shape data.

The analysis unit 42 applies analysis processing to retinal layers to be analyzed based on the determination result of the determination unit 43. Note that this embodiment will explain a case of macula analysis of a myopia as the three-dimensional shape analysis processing. The analysis result generation unit 45 generates various data required to present the analysis result (information indicating states of retinal layers). The shape data generation unit 46 aligns a plurality of tomographic images obtained by imaging, thereby generating three-dimensional shape data. That is, the three-dimensional shape data is generated based on layer information of retinal layers.

The alignment unit 47 performs alignment between the analysis result and fundus image, that between fundus images, and the like. The instruction unit 34 instructs information such as imaging parameters according to the imaging mode set in the tomography apparatus 20.

The example of the arrangement of the image processing system 10 has been described. Note that the functional units arranged in the aforementioned apparatuses need not always be implemented, as shown in FIG. 1, and all or some of these units need only be implemented in any apparatus in the system. For example, in FIG. 1, the external storage device 52, display device 53, and input device 54 are arranged outside the image processing apparatus 30. However, these devices may be arranged inside the image processing apparatus 30. Also, for example, the image processing apparatus and tomography apparatus 20 may be integrated.

An example of a tomographic image capturing screen 60 displayed on the display device 53 shown in FIG. 1 will be described below with reference to FIG. 2. Note that this screen is displayed when a tomographic image is to be captured.

The tomographic image capturing screen 60 includes a tomographic image display field 61, fundus image display field 62, combo box 63 used to set an imaging mode, and capture button 64 used to instruct to capture an image. Note that reference numeral 65 in the fundus image display field 62 denotes a mark which indicates an imaging region, and is superimposed on a fundus image. Reference symbol M denotes a macular region; D, an optic papilla; and V, a blood vessel.

The combo box 63 allows the user to set, for example, an imaging mode for myopia analysis of (a macular region) or that for non-myopia analysis of (the macular region). That is, the combo box 63 has an imaging mode selection function. In this case, the imaging mode for myopia analysis is set.

The tomographic image display field 61 displays a tomographic image of a fundus. Reference numeral L1 denotes an inner limiting membrane (ILM); L2, a boundary between a nerve fiber layer (NFL) and ganglion cell layer (GCL); and L3, an inner segment outer segment junction (ISOS) of a photoreceptor cell. Also, reference numeral L4 denotes a pigmented retinal layer (RPE); and L5, a Bruch's membrane (BM). The aforementioned detection unit 41 detects any of boundaries of L1 to L5.

Figure 3A:
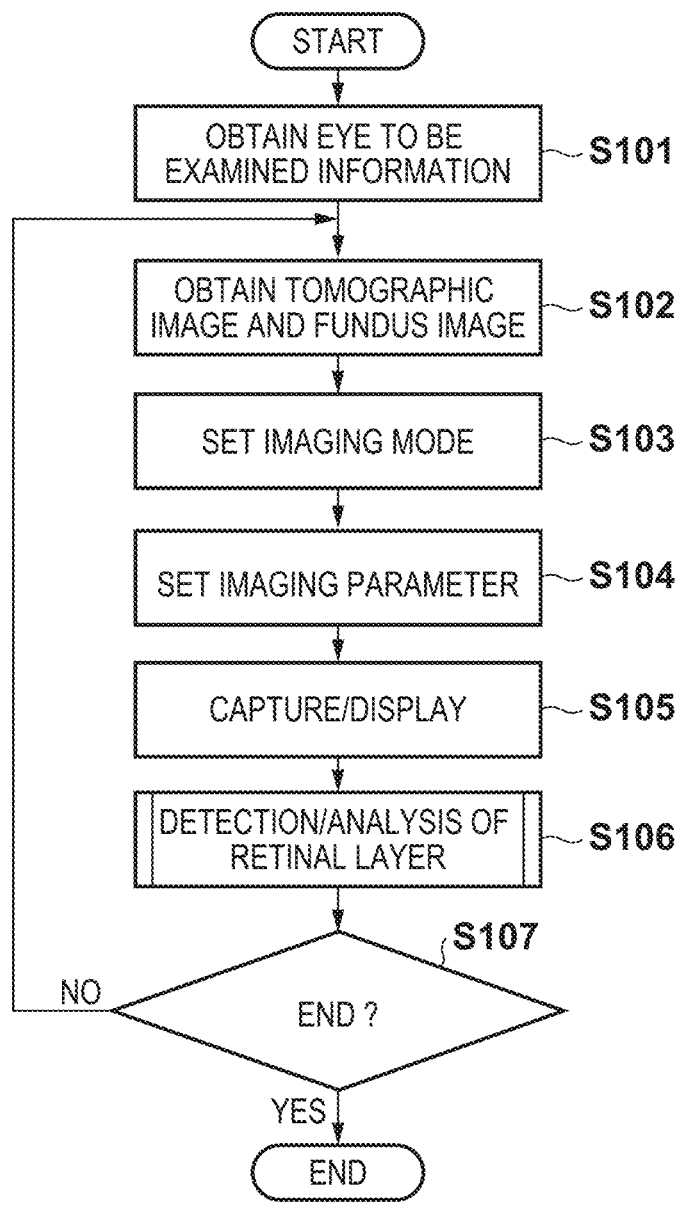
FIGS. 3A and 3B are flowcharts showing an example of the sequence of processing of an image processing apparatus 30 shown in FIG. 1.

An example of the sequence of processing of the image processing apparatus 30 shown in FIG. 1 will be described below with reference to FIGS. 3A and 3B. The sequence of the overall processing at the time of capturing of a tomographic image will be described first with reference to FIG. 3A.

[Step S101]

The image processing apparatus 30 externally obtains a patient identification number as information required to identify an eye to be examined. Then, the image processing apparatus 30 obtains information related to the eye to be examined, which information is held by the external storage device 52, based on the patient identification number, and stores the obtained information in the storage unit 32.

[Step S102]

The image processing apparatus 30 instructs the image obtaining unit 31 to obtain a fundus image from the fundus image capturing device 51 and a tomographic image from the tomography apparatus 20 as pre-scan images used to confirm an imaging position at the imaging timing.

[Step S103]

The image processing apparatus 30 sets an imaging mode. The imaging mode is set based on a choice of the operator from the combo box 63 used to set the imaging mode, as described in FIG. 2. A case will be described below wherein imaging is to be done in the imaging mode for myopia analysis.

[Step S104]

The image processing apparatus 30 instructs the instruction unit 34 to issue an imaging parameter instruction according to the imaging mode set from the combo box 63 to the tomography apparatus 20. Thus, the tomography apparatus 20 controls the parameter setting unit 23 to set the imaging parameters according to the instruction. More specifically, the image processing apparatus 30 instructs to set at least one of the position of the vision fixation lamp, scanning range, and scanning pattern, and coherence gate position.

The parameter settings in the imaging mode for myopia analysis will be described below. In a parameter setting of the position of the vision fixation lamp, the position of the vision fixation lamp 24 is set to be able to capture an image of the center of a macular region. The image processing apparatus 30 instructs the driving control unit 22 to control the light-emitting diodes of the indication unit 24a according to the imaging parameters. Note that in case of an apparatus with an arrangement which allows to assure a sufficiently broad imaging range, the position of the vision fixation lamp 24 may be controlled to set the center between a macular region and optic papilla as that of imaging. The reason why such control is executed is to capture an image of a region including a macular region so as to execute shape analysis of retinal layers in a myopia.

In a parameter setting of the scanning range, for example, a range of 9 to 15 mm is set as limit values of an imaging range of the apparatus. These values are merely an example, and may be changed as needed according to the specifications of the apparatus. Note that the imaging range is a broader region so as to detect shape change locations without any omission.

In a parameter setting of the scanning pattern, for example, a raster scan or radial scan is set so as to be able to capture a three-dimensional shape of retinal layers.

In a parameter setting of the coherence gate position, the gate position is set so as to allow imaging based on the EDI method. In a high myopia, a degree of curvature of retinal layers becomes strong, and an image of retinal layers is unwantedly captured beyond an upper portion side of a tomographic image. In this case, retinal layers beyond the upper portion of the tomographic image are folded back and appear in the tomographic image, and such parameter setting is required to prevent this. Note that when the SS-OCT of the large invasion depth is used as the tomography apparatus 20, if the position of retinal layers is distant from the gate position, a satisfactory tomographic image can be obtained. Hence, imaging based on the EDI method is not always done.

[Step S105]

The image processing apparatus 30 instructs the instruction unit 34 to issue an imaging instruction of the eye to be examined to the tomography apparatus 20. This instruction is issued, for example, when the operator presses the capture button 64 of the tomographic image capturing screen 60 via the input device 54. In response to this instruction, the tomography apparatus 20 controls the driving controller 22 based on the imaging parameters set by the parameter setting unit 23. Thus, the galvanometer mirror 21 is activated to capture a tomographic image.

As described above, the galvanometer mirror 21 includes an X-scanner for a horizontal direction, and a Y scanner for a vertical direction. For this reason, by changing the directions of these scanners, respectively, a tomographic image can be captured along the horizontal direction (X) and vertical direction (Y) on an apparatus coordinate system. By simultaneously changing the directions of these scanners, a scan can be made in a synthesized direction of the horizontal and vertical directions. Hence, imaging along an arbitrary direction on a fundus plane can be done. At this time, the image processing apparatus 30 instructs the display control unit 35 to display the captured tomographic image on the display device 53. Thus, the operator can confirm the imaging result.

[Step S106]

The image processing apparatus 30 instructs the image processing unit 33 to detect/analyze retinal layers from the tomographic image stored in the storage unit 32. That is, the image processing apparatus 30 applies detection/analysis processing of retinal layers to the tomographic image captured in the process of step S105.

[Step S107]

The image processing apparatus 30 determines whether or not to end imaging of tomographic images. This determination is made based on an instruction from the operator via the input device 54. That is, the image processing apparatus 30 determines whether or not to end imaging of tomographic images based on whether or not the operator inputs an end instruction.

When the imaging end instruction is input, the image processing apparatus 30 ends this processing. On the other hand, when imaging is to be continued without ending processing, the image processing apparatus 30 executes processes in step S102 and subsequent steps.

Note that when the operator manually modifies the detection result of retinal layers and the positions of a fundus image and map by processes of steps S206 and S209 (to be described later), the image processing apparatus 30 saves the imaging parameters changed according to such modifications in the external storage device 52 upon ending imaging. At this time, a confirmation dialog as to whether or not to save the changed parameters may be displayed to issue an inquiry about whether or not to change the imaging parameters to the operator.

The detection/analysis processing of retinal layers in step S106 of FIG. 3A will be described below with reference to FIG. 3B.

[Step S201]

When the detection/analysis processing of retinal layers is started, the image processing apparatus 30 instructs the detection unit 41 to detect retinal layers from a tomographic image. This processing will be practically described below using a tomographic image (display field 61) shown in FIG. 2. In case of a macular region, the detection unit 41 applies a median filter and Sobel filter to the tomographic image to generate images (to be respectively referred to as a median image and Sobel image hereinafter).

Subsequently, the detection unit 41 generates profiles for each A-scan from the generated median image and Sobel image. A luminance value profile is generated from the median image, and a gradient profile is generated from the Sobel image. Then, the detection unit 41 detects peaks in the profile generated from the Sobel image. Finally, the detection unit 41 refers to the profile of the median image corresponding to portions before and after the detected peaks and those between adjacent peaks, thus detecting boundaries of respective regions of the retinal layers. That is, L1 (ILM), L2 (boundary between the NFL and GCL), L3 (ISOS), L4 (RPE), L5 (BM), and the like are detected. Note that the following description of this embodiment will be given under the assumption that an analysis target layer is the RPE.

[Step S202]

The image processing unit 30 controls the determination unit 43 to determine whether or not to execute three-dimensional shape analysis of the retinal layer. More specifically, if imaging is done in the imaging mode for myopia analysis, it is determined that the three-dimensional shape analysis of the retinal layer is to be executed. If imaging is done without using the myopia analysis mode (in the imaging mode for non-myopia analysis), it is determined that the three-dimensional shape analysis is not to be executed. In this case, analysis based on the detection result of the detection unit 41 is performed (analysis without using the three-dimensional shape data). Note that even in the imaging mode for myopia analysis, it is determined based on a tomographic image whether or not a macular region is included in the tomographic image. If no macular region is included in the tomographic image (for example, only an optic papilla is included), it may be determined that (three-dimensional) shape analysis of the retinal layer is not to be executed.

The following description of this embodiment will be given under the assumption that a series of processes from imaging to analysis are executed in the image processing system 10 which integrates the tomography apparatus 20 and image processing apparatus 30. However, the present invention is not limited to this. That is, the image processing apparatus 30 need only execute shape analysis of a retinal layer upon reception of a tomographic image of a macular region using a scanning pattern required to obtain a three-dimensional shape, and such integrated system need not always be adopted. For this reason, the image processing apparatus 30 can execute shape analysis of a retinal layer for a tomographic image captured by an apparatus other than the tomography apparatus 20 based on information at the time of imaging. However, when shape analysis is not required, the shape analysis processing may be skipped.

[Step S203]

The image processing apparatus 30 instructs the shape data generation unit 46 to generate three-dimensional shape data. The three-dimensional shape data is generated to execute shape analysis based on the detection result of the retinal layer in the process of step S201.

In this case, when the scanning pattern at the time of imaging is, for example, a raster scan, a plurality of adjacent tomographic images are aligned. In alignment of tomographic images, for example, an evaluation function which represents a similarity between two tomographic images is defined in advance, and tomographic images are deformed to maximize this evaluation function value.

As the evaluation function, for example, a method of evaluating pixel values (for example, a method of making evaluation using correlation coefficients) may be used. As the deformation processing of images, processing for making translation and rotation using affine transformation may be used. After completion of the alignment processing of the plurality of tomographic images, the shape data generation unit 46 generates three-dimensional shape data of a layer as a shape analysis target. The three-dimensional shape data can be generated by preparing, for example, 512×512×500 voxel data, and assigning labels to positions corresponding to coordinate values of layer data of the detected retinal layer.

On the other hand, when the scanning pattern at the time of imaging is a radial scan, the shape data generation unit 46 aligns tomographic images, and then generates three-dimensional shape data in the same manner as described above. However, in this case, alignment in a depth direction (Z direction of the tomographic image (display field 61) shown in FIG. 2) is made using only region information near the centers of adjacent tomographic images. This is because in case of the radial scan, even adjacent tomographic images include coarse information at two ends compared to the vicinity of each center thereof, shape changes are large, and such information is not used as alignment information. As the alignment method, the aforementioned method can be used. After completion of the alignment processing, the shape data generation unit 46 generates three-dimensional shape data of a layer as a shape analysis target.

In case of the radial scan, for example, 512×512×500 voxel data are prepared, and layer data as a shape analysis target of respective tomographic images are evenly circularly rotated and expanded. After that, in the expanded layer data, interpolation processing is executed between adjacent shape data in the circumferential direction. With the interpolation processing, shape data at non-captured positions are generated. As the interpolation processing method, processing such as linear interpolation or nonlinear interpolation may be applied. The three-dimensional shape data can be generated by assigning labels to positions corresponding to coordinate values obtained by interpolating between layer data of the detected retinal layer.

Note that numerical values of the voxel data described above are merely an example, and can be changed as needed depending on the number of A-scans at the time of imaging and the memory size of the apparatus which executes the processing. Since large voxel data have a high resolution, they can accurately express shape data. However, such voxel data suffers a low execution speed, and have a large memory consumption amount. On the other hand, although small voxel data have a low resolution, they can assure a high execution speed and have a small memory consumption amount.

[Step S204]

The image processing apparatus 30 instructs the analysis unit 42 to execute the three-dimensional shape analysis of the retinal layer. As the shape analysis method, a method of measuring an area and volume of the retinal layer will be exemplified below.

Figure 4:
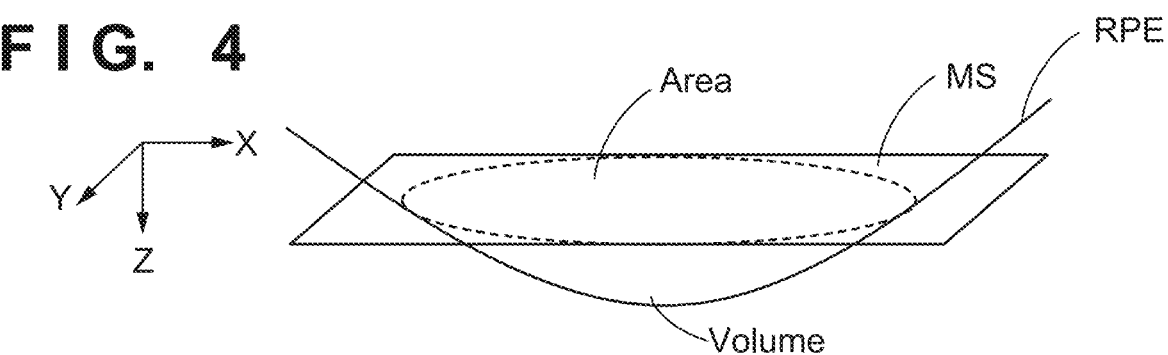
FIG. 4 is a view for explaining an overview of three-dimensional shape analysis processing.

This processing will be described below with reference to FIG. 4. FIG. 4 illustrates three-dimensional shape data (RPE), measurement surface (MS), area (Area), and volume (Volume).

An area measurement will be described first. In the three-dimensional shape data of the RPE generated in the process of step S203, a flat (planar) measurement surface (MS) is prepared at a place of layer data located at the deepest portion in the Z direction (optical axis direction). Then, the measurement surface (MS) is moved at given intervals in a shallow direction (an origin direction of the Z-axis) from there. When the measurement surface (MS) is moved from the deep portion of the layer in the shallow direction, it traverses a boundary line of the RPE.

An area (Area) is obtained by measuring an internal planar region bounded by the measurement surface (MS) and the boundary line with the RPE. More specifically, the area (Area) is obtained by measuring an area of an intersection region between the measurement surface (MS) and boundary line with the RPE. In this manner, the area (Area) is a cross-sectional area of the three-dimensional retinal layer shape data. Upon measuring a cross-sectional area at a position of a reference portion, when a curvature of the retinal layer is strong, a small area is obtained; when the curvature of the retinal layer is moderate, a large area is obtained.

A volume (Volume) can be obtained by measuring a whole internal region bounded by the measurement surface (MS) and the boundary line with the RPE using the measurement surface (MS) used in the measurement of the area (Area). Upon measuring a volume in a downward direction along the Z direction from a position of a reference position, when a curvature of the retinal layer is strong, a large volume is obtained; when the curvature of the retinal layer is moderate, a small volume is obtained. In this case, the reference position can be set at an Bruch's membrane opening position with reference to a portion. Alternatively, a given height such as 100 μm or 500 μm from the deepest position of the RPE may be used as a reference. Note that when the number of voxels included in a region to be measured is counted upon measuring the area or volume, the area or volume is calculated by multiplying the number of voxels by a physical size per voxel.

[Step S205]

After the shape analysis, the image processing apparatus 30 instructs the analysis result generation unit 45 to generate an analysis result (for example, a map, graph, or numerical value information) based on the three-dimensional shape analysis result.

A case will be described below wherein a contour line map is generated as the three-dimensional shape analysis result. The contour line map is used when the measurement results of the area and volume are to be displayed.

Figure 5A:
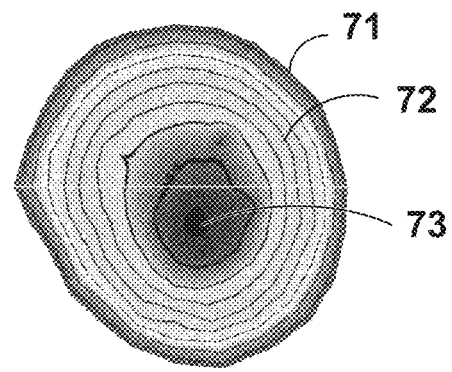
FIGS. 5A to 5C are views for explaining an overview of three-dimensional shape analysis processing.

FIG. 5A shows an example of a contour line map 71. The contour line map 71 is an overall contour line map. Reference numeral 72 denotes contour lines drawn at given intervals; and 73, a portion located at the deepest portion in the Z direction of the three-dimensional retinal layer shape data.

When the contour line map 71 is to be generated, a lookup table for a contour line map is prepared, and the map is color-coded according to the volumes with reference to the table. In this case, the lookup table for the contour line map may be prepared according to the volumes. Thus, the operator can recognize changes of the shape and volume at a glance on the map.

More specifically, the contour lines 72 are drawn at given intervals to have the portion 73 in FIG. 5A as a bottom, and the colors of the map are set according to the volumes. For this reason, when the height (depth) of the measurement surface is changed from the portion located at the deepest position in the Z direction, the operator can recognize how to increase a volume. More specifically, when it is set to color-code 1 mm$^3$ as blue and 2 mm$^3$ as yellow, the operator can recognize the relationship between the shape and volume by checking whether blue corresponds to the height (depth) of 100 μm or 300 μm of the measurement surface from the portion located at the deepest position in the Z direction. Therefore, the operator can recognize the overall volume upon measuring the shape of the retinal layer to be measured by confirming a color of an outermost contour of the map.

Also, the operator can confirm a volume value corresponding to a height (depth) by confirming a color near each internal contour line. Note that the lookup table used upon setting colors of the contour line map may be prepared according to areas in place of the volumes. Alternatively, the lookup table may be prepared according to heights (depths) to the portion 73 located at the deepest position in the Z direction. Although not shown, numerical values may be displayed together on respective contour lines so as to allow the operator to understand the heights (depths) of the contour lines. As an interval of a distance which expresses a contour line, for example, a 100-μm interval along the Z direction is set. Note that the contour line map may be either a color or grayscale map, but visibility is high in case of the color map.

Figure 5B:
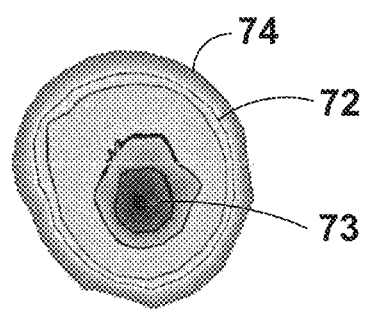

An outer shape size of the contour line map changes depending on the height (depth) from the portion located at the deepest position in the Z direction to the measurement surface (MS). FIG. 5B shows an example of a contour line map 74 when the height (depth) of the measurement surface (MS) is changed.

A case in which a curvature of the retinal layer is to be measured as the three-dimensional shape analysis will be described below using the tomographic image (display field 61) shown in FIG. 2. In the following description, a case will be explained wherein the abscissa is defined as an x-coordinate axis, the ordinate is defined as a z-coordinate axis, and a curvature of a boundary line of the layer (RPE) as an analysis target is calculated. A curvature κ can be obtained by calculating, at respective points of the boundary line:

$$\kappa = \frac{\frac{d^2z}{dx^2}}{\left(1+\left(\frac{dz}{dx}\right)\right)^{\frac{3}{2}}} \quad (1)$$

The sign of the curvature κ reveals that the shape is upward or downward convex, and the magnitude of a numeral value reveals a curved degree of the shape. For this reason, if upward convex is expressed by "+" and downward convex is expressed by "−", if each tomographic image includes a − region, + region, and − region as the signs of the curvature, the layer has a W-shape.

Note that the case has been explained wherein the curvature of the boundary line of the tomographic image is calculated in this case. However, the present invention is not limited to such specific curvature calculation, and three-dimensional curvatures may be calculated from the three-dimensional shape data. In this case, after the shape analysis, the image processing apparatus 30 instructs the analysis result generation unit 45 to generate a curvature map based on the analysis result.

Figure 5C:
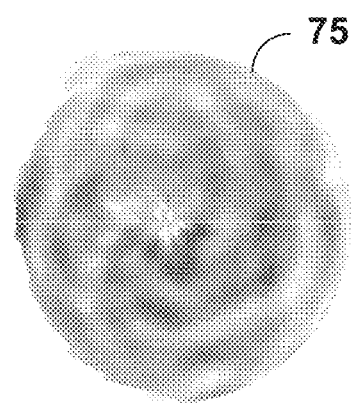

FIG. 5C shows an example of the curvature map. In this case, a portion having a strong curvature is expressed by a dark color, and that having a moderate curvature is expressed by a light color. More specifically, the color density is changed depending on the curvatures. Note that colors to be set in the curvature map may be changed depending on positive and negative curvature values with reference to a curvature value=0. Thus, the operator can recognize whether or not the retina shape is smooth and whether it is an upward or downward convex shape by checking the map.

[Step S206]

The image processing apparatus 30 instructs the display control unit 35 to display a tomographic image, the detection result of the layer (RPE) detected by the detection unit 41, and various shape analysis results (map, graph, and numerical value information) generated by the analysis result generation unit 45 on the display device 53.

Figure 6:
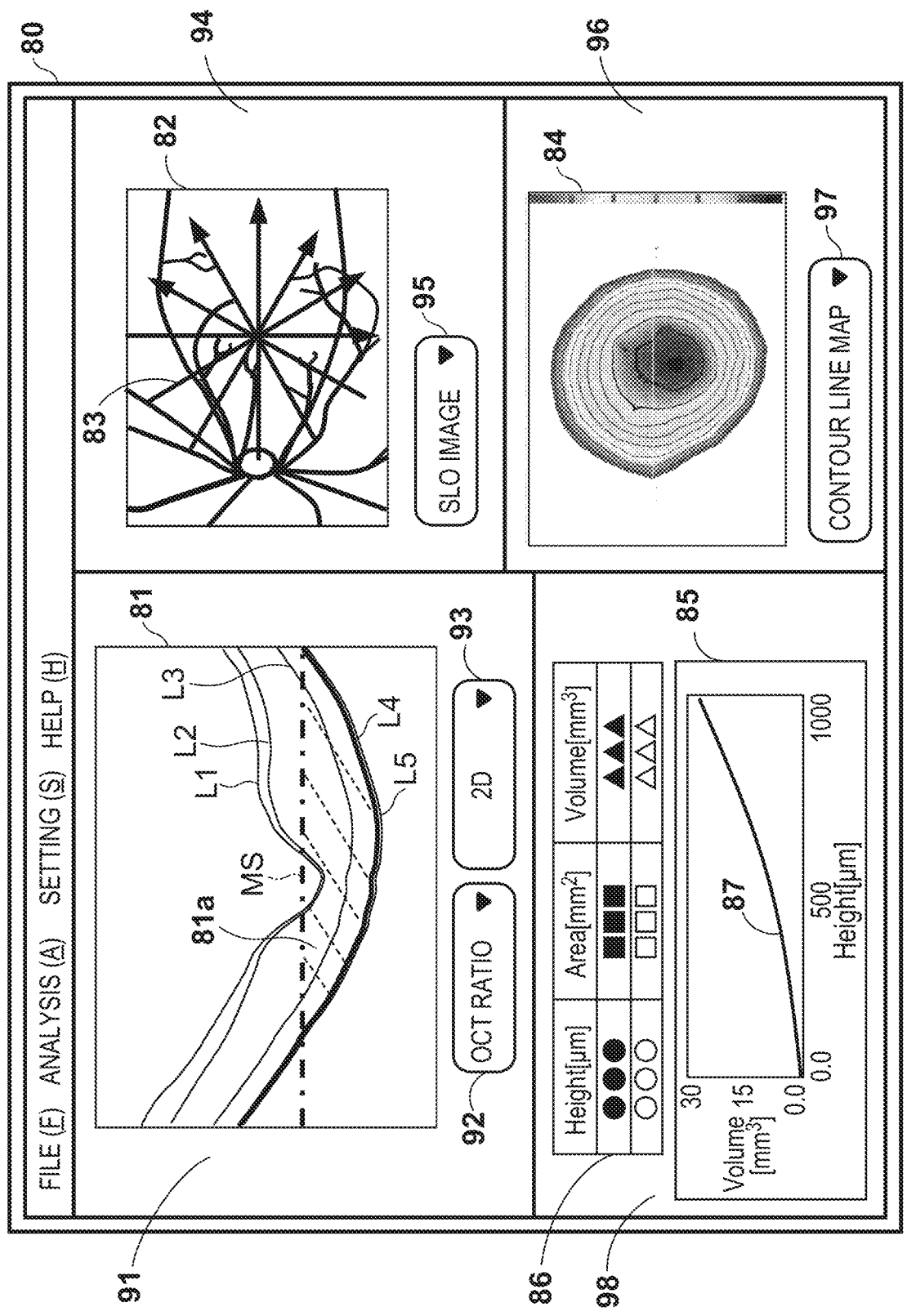
FIG. 6 is a view showing an example of a tomographic image observation screen 80.

FIG. 6 shows an example of a tomographic image observation screen 80 displayed on the display device 53 shown in FIG. 1. This screen is displayed after completion of the analysis of tomographic images (that is, it is displayed by the process of step S206).

The tomographic image observation screen 80 includes a tomographic image display section 91 including a tomographic image display field 81, and a fundus image display section 94 including a fundus image display field 82. The tomographic image observation screen 80 also includes a first analysis result display section 96 including a first analysis result 84, and a second analysis result display section 98 including second analysis results 85 and 86.

Details of the tomographic image display section 91 including the tomographic image display field 81 will be described first. The tomographic image display field 81 displays segmentation results (L1 to L5) obtained by detecting the respective layers of the retinal layers and the measurement surface (MS) which are superimposed on the captured tomographic image. The tomographic image display field 81 highlights the segmentation result of the retinal layer (RPE (L4) in this embodiment) as an analysis target.

On the tomographic image display field 81, a hatched region 81a bounded by the measurement surface (MS) and the retinal layer (RPE (L4)) as an analysis target is a measurement target region of the area and volume. At this time, on the hatched region 81a, a color according to the volume measurement result is displayed to have a predetermined transparency α. The same color to be set as that in the lookup table for the contour line map can be used. The transparency α is, for example, 0.5.

A combo box 92 is provided to allow the operator to select whether the tomographic image is displayed at an OCT ratio or 1:1 ratio. In this case, the OCT ratio is that expressed by a resolution in the horizontal direction (X direction) and that in the vertical direction (Y direction), which are obtained based on the number of A-scans at the time of imaging. The 1:1 ratio is that which adjusts a physical size per pixel in the horizontal direction and that per pixel in the vertical direction, which are obtained based on the number of A-scans used to capture a given range (mm).

A combo box 93 is provided to allow the operator to switch a two-dimensional (2D)/three-dimensional (3D) display mode. In the 2D display mode, one slice of the tomographic image is displayed; in the 3D display mode, the three-dimensional shape of the retinal layers generated from the boundary line data of the retinal layers is displayed.

Figure 7A:
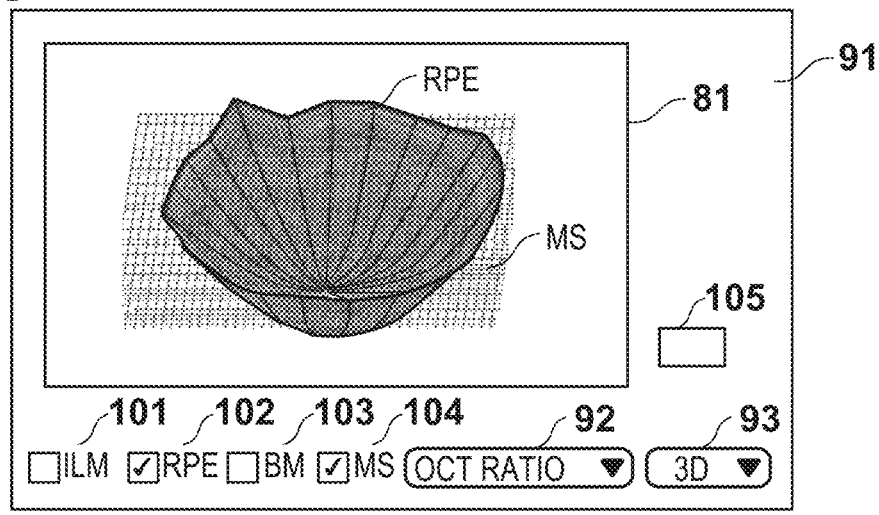
FIGS. 7A to 7C are views showing an example of respective components of the tomographic image observation screen 80.
Figure 7B:
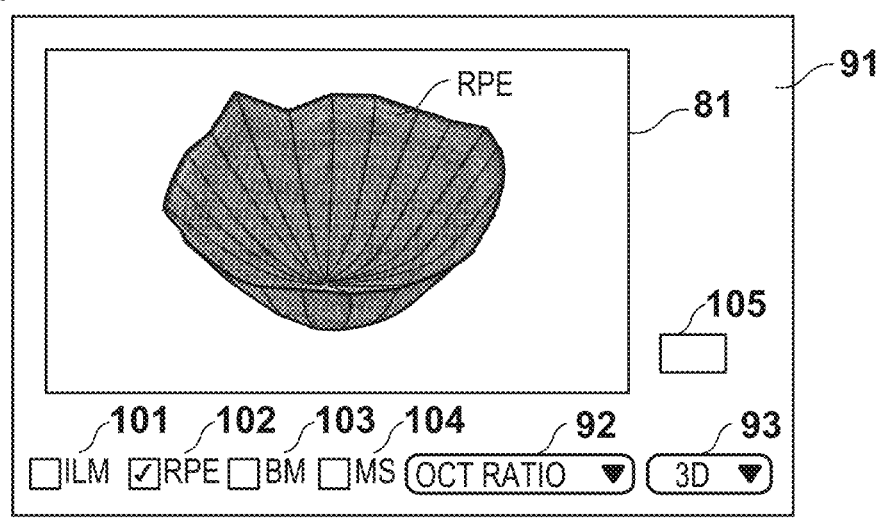
Figure 7C:
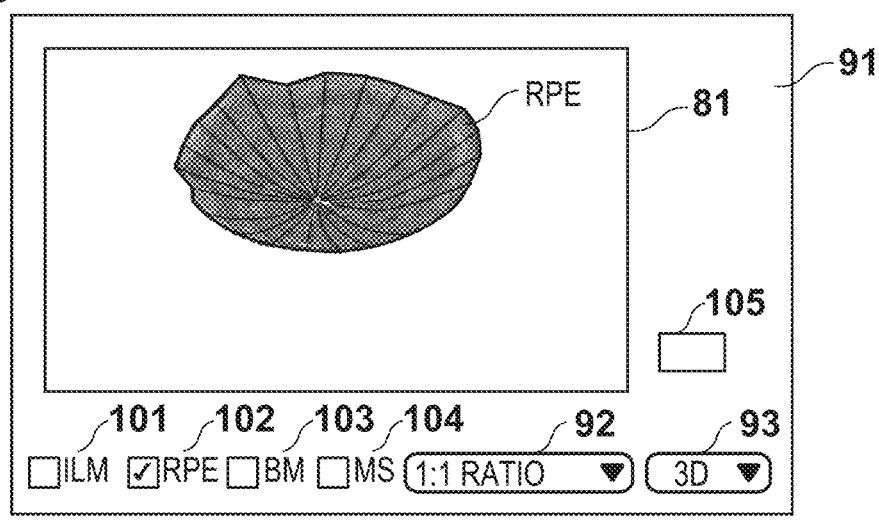

More specifically, when the operator selects the 3D display mode at the combo box 93, a tomographic image shown in one of FIGS. 7A to 7C is displayed in the tomographic image display field 81.

FIG. 7A shows a mode when the RPE is displayed at the OCT ratio in the 3D display mode. In this case, the measurement surface (MS) is simultaneously displayed in the 3D display mode.

In this case, check boxes 101 to 104 corresponding to the respective layers of the retina are displayed below the tomographic image display field 81. More specifically, the check boxes corresponding to the ILM, RPE, BM, and MS are displayed, and the operator can switch display/non-display states of the respective layers using these check boxes.

When the measurement surface (MS) is expressed by a plane, its transparency α assumes a value which is larger than 0 and is smaller than 1. In a state in which the transparency is 1, and when the retinal layer shape and measurement surface are overlaid, the shape is unwantedly covered, and the three-dimensional shape of the retinal layers cannot be recognized from the upper side. Alternatively, the measurement surface (MS) may be expressed by a grid pattern in place of the plane. In case of the grid pattern, the transparency α of the measurement surface (MS) may be set to be 1. As for a color of the measurement surface (MS), a color according to a measurement value (area or volume) at the location of the measurement surface (MS) need only be selected with reference to the lookup table for the contour line map.

In this case, the operator can move the position of the measurement surface (MS) via the input device 54. For this reason, when the position of the measurement surface (MS) is changed, the image processing apparatus 30 changes the contour line map shape in synchronism with that change, as described in FIGS. 5A and 5B.

A text box 105 is an item used to designate a numerical value. The operator inputs, to the text box 105, a numerical value indicating a height (depth) of the measurement surface (MS) from the portion at the deepest position in the Z direction via the input device 54. For example, when the operator inputs a numerical value such as 100 µm or 300 µm, the measurement surface (MS) is moved to that position, and the contour line map is changed accordingly. Thus, the operator can simultaneously recognize the position in the three-dimensional shape and the contour line map at that time, and can also recognize a volume value and area value at that time.

As another example, the operator may input a volume value in the text box 105. In this case, when the operator inputs a numerical value such as 1 mm$^3$ or 2 mm$^3$, he or she can simultaneously recognize the position in the three-dimensional shape and the contour line map at that time, which correspond to that volume. Furthermore, the operator can also recognize a height (depth) of the measurement surface (MS) from the portion at the deepest position in the Z direction at that time.

Subsequently, FIG. 7B shows a display mode when the measurement surface (MS) is set in a non-display state. Other display items are the same as those in FIG. 7A. In case of FIG. 7B, the check box 102 is selected to display the RPE alone. In this manner, only the three-dimensional shape of a fundus can be displayed.

FIG. 7B shows the 3D display mode of the RPE at the OCT ratio, while FIG. 7C shows a mode when the RPE is displayed at the 1:1 ratio in the 3D display mode. That is, the 1:1 ratio is selected at the combo box 92.

Note that since this embodiment has explained the RPE as the analysis target, when the 2D/3D display mode is switched at the combo box 93, the RPE shape is displayed in the 2D/3D display mode. However, the present invention is not limited to this. For example, when the Bruch's membrane (BM) is selected as an analysis target, the Bruch's membrane (BM) is displayed in the 2D/3D display mode.

In this case, the position measured by the measurement surface may be schematically displayed on the tomographic image display field 81. A display mode in this case will be described below with reference to FIGS. 8A to 8D.

Figure 8A:
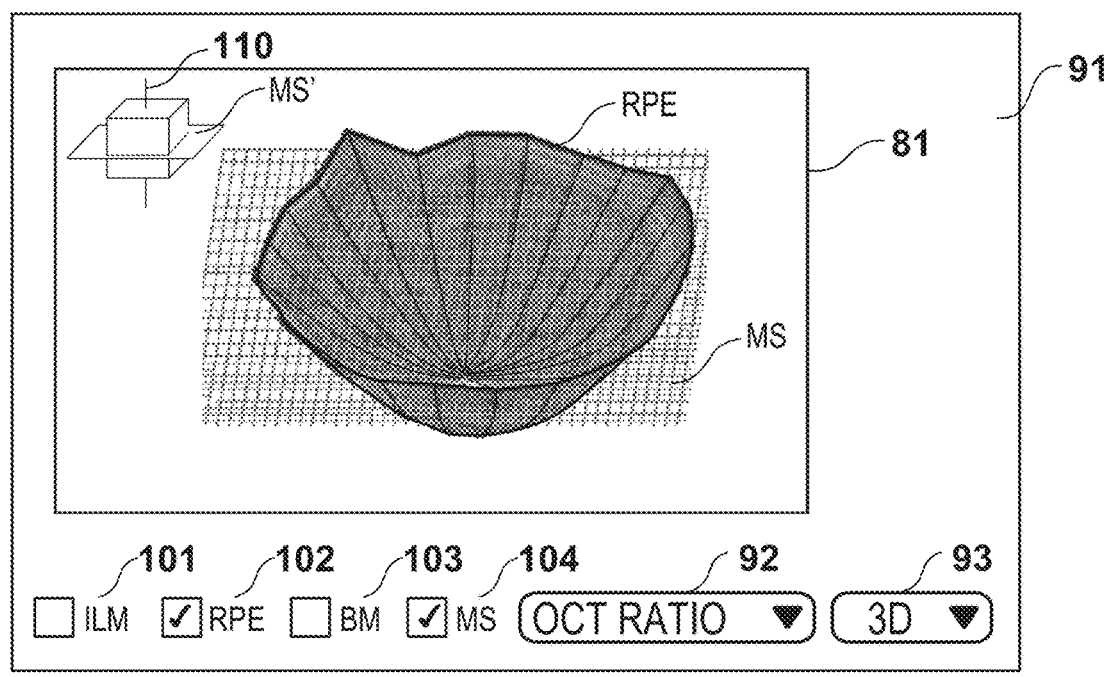
FIGS. 8A to 8D are views showing an example of respective components of the tomographic image observation screen 80.

FIG. 8A shows a mode in which an object 110 indicating the position measured by the measurement surface in the currently displayed tomographic image is superimposed on the tomographic image. Reference symbol MS' denotes a measurement surface (schematic measurement surface) on the object 110. The three-dimensional shape of the retinal layer is rotated in the upper, lower, right, and left directions by an instruction input by the operator via the input device 54. For this reason, in order to allow the operator to recognize the positional relationship between the measurement surface (MS) and retinal layer, the object 110 and schematic measurement surface MS' present an index of the positional relationship.

Note that when the operator changes the positional relationship between the object 110 and schematic measurement surface MS' via the input device 54, the displayed three-dimensional shape of the retinal layer is also changed in synchronism with that change. In this case, since the region of the retinal layer as the analysis target is also changed, the first analysis result 84 and second analysis results 85 and 86 are changed in synchronism with that change.

Figure 8B:
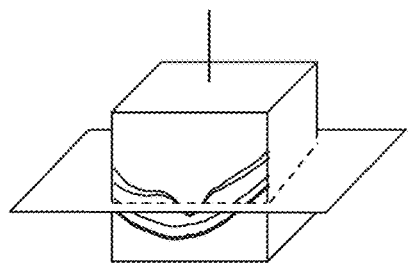
Figure 8C:
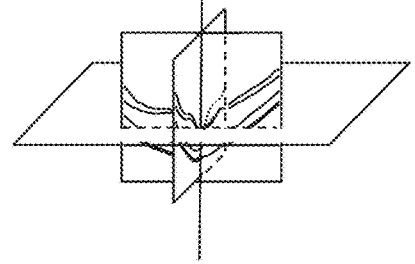
Figure 8D:
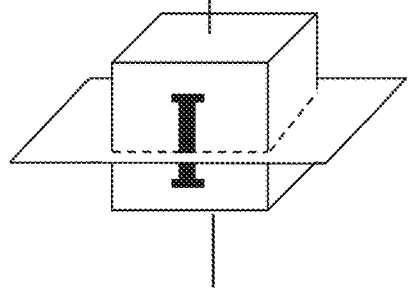

Some display modes of the object 110 will be exemplified below. For example, as shown in FIGS. 8B and 8C, tomographic images corresponding to respective section positions may be displayed. In this case, in the object 110, tomographic images at vertical and horizontal positions, which intersect the central position in consideration of a three-dimensional shape, are displayed. Alternatively, as shown in FIG. 8D, an abbreviation such as "S" or "I" indicating "superior" or "inferior" may be displayed.

Details of the fundus image display section 94 including the fundus image display field 82 shown in FIG. 6 will be described below. On The fundus image display field 82, an imaging position and its scanning pattern mark 83 are superimposed on the fundus image. The fundus image display section 94 is provided with a combo box 95 which allows the operator to switch a display format of the fundus image. In this case, an SLO image is displayed as the fundus image.

A case will be described below with reference to FIGS. 9A and 9B wherein the operator switches the display format of the fundus image from the combo box 95. In this case, a case in which "SLO image+map" are simultaneously displayed and a case in which "fundus photo (second fundus image)+SLO image (first fundus image)+map" are simultaneously displayed as the display formats of the fundus image will be exemplified. Note that the SLO image (first fundus image) can be a two-dimensional fundus image captured simultaneously with a tomographic image, and for example, it may be an integrated image generated by integrating tomographic images in the depth direction. The fundus photo (second fundus image) may be a two-dimensional fundus image captured at a timing different from a tomographic image, and for example, a contrast radiographic image or the like may be used.

Figure 9A:
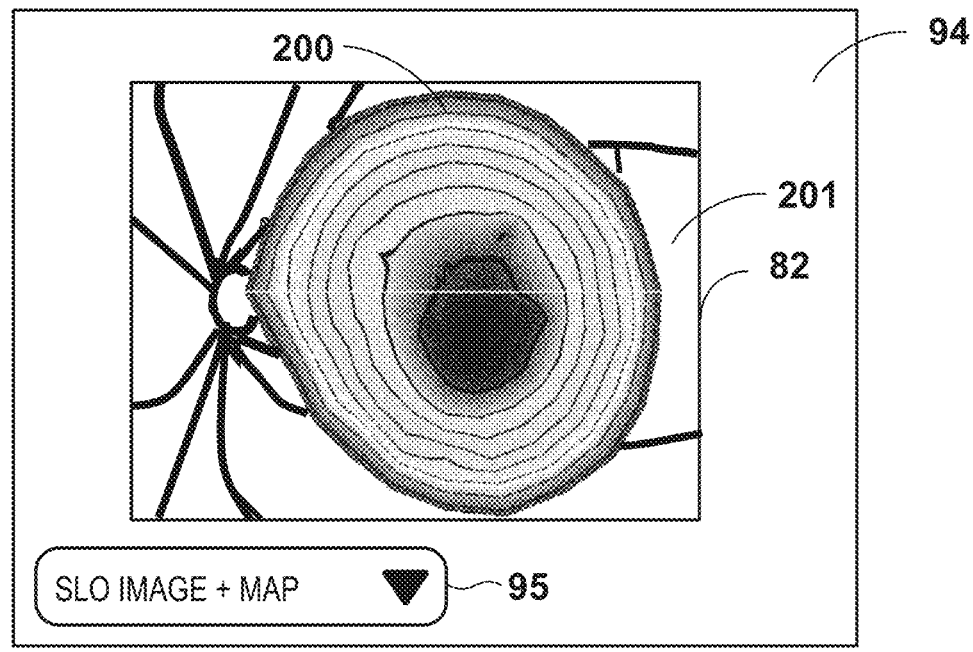
FIGS. 9A and 9B are views showing an example of respective components of the tomographic image observation screen 80.

FIG. 9A shows a display mode when the operator selects "SLO image+map" from the combo box 95. Reference numeral 201 denotes an SLO image; and 200, a map. The SLO image 201 and map 200 are aligned by the alignment unit 47 described using FIG. 1. The SLO image and map are aligned by setting the position and size of the map based on the position of the vision fixation lamp and the scanning range at the time of imaging.

When a superimposing result of the map 200 on the SLO image 201 is displayed as the fundus image, the transparency α of the SLO image 201 to be displayed is set to be 1, and that of the map 200 to be displayed is set to be smaller than 1 (for example, 0.5). These parameters of the transparencies α are those to be set when the operator selects target data for the first time. The operator can change these parameters via the input device 54 as needed. The parameters changed by the operator are stored in, for example, the external storage device 52. When the same target data is opened for the next or subsequent time, display processing is performed according to the parameters previously set by the operator.

Figure 9B:
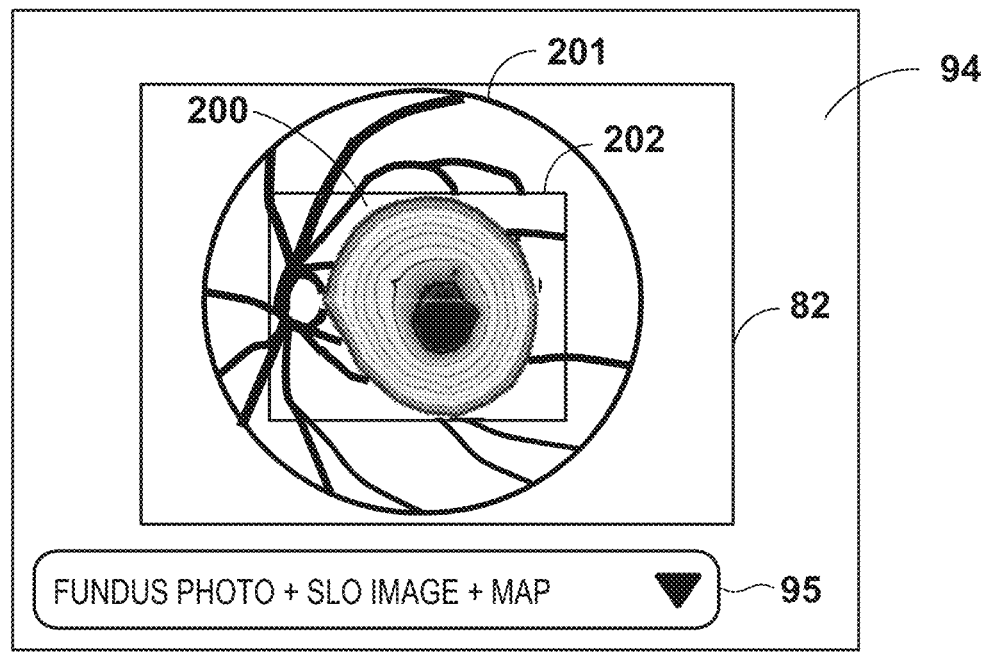

Subsequently, FIG. 9B shows a display mode when the operator selects "fundus photo+SLO image+map" from the combo box 95. Reference numeral 202 denotes a fundus photo (second fundus image).

In this case, in order to superimpose the map 200 on the fundus photo 202 (that is, to superimpose the map 200 on the second fundus image), the SLO image 201 is used. This is because the fundus photo 202 is captured at a timing different from a tomographic image, and the imaging position and range cannot be recognized based on the map 200 alone. Hence, using the SLO image 201, the fundus photo 202 and map 200 can be aligned. The fundus photo 202 and SLO image 201 are aligned by the alignment unit 47 described using FIG. 1.

As the alignment method, for example, a blood vessel feature may be used. As a detection method of blood vessels, since each blood vessel has a thin linear structure, blood vessels are extracted using a filter used to emphasize the linear structure. As the filter used to emphasize the linear structure, when a line segment is defined as a structural element, a filter which calculates a difference between an average value of image density values in the structural element and that in a local region which surrounds the structural element may be used. Of course, the present invention is not limited to such specific filter, and a difference filter such as a Sobel filter may be used. Alternatively, eigenvalues of a Hessian matrix may be calculated for each pixel of a density value image, and a line segment-like region may be extracted based on combinations of two eigenvalues obtained as calculation results. The alignment unit 47 aligns the fundus photo 202 and SLO image 201 using blood vessel position information detected by these methods.

Since the SLO image 201 and map 200 can be aligned by the aforementioned method, the fundus photo 202 and map 200 can also be consequently aligned. When a superimposing result of the map 200 on the fundus photo 202 is displayed on the display field 82 of the fundus image display section 94, the transparency α of the fundus photo 202 to be displayed is set to be 1. Also, the transparency of the SLO image 201 to be displayed and that of the map 200 to be displayed are set to be smaller than 1 (for example, 0.5). Of course, the values of the transparencies α of the SLO image 201 and map 200 need not always be the same. For example, the value of the transparency α of the SLO image 201 may be set to be 0.

Note that when an eye to be examined is a diseased eye, the alignment processing by the alignment unit 47 may often fail. An alignment failure is determined when a maximum similarity does not become equal to or larger than a threshold upon calculation of an inter-image similarity. Even when the maximum similarity becomes equal to or larger than the threshold, the end of alignment processing at an anatomically abnormal position determines a failure. In this case, the SLO image 201 and map 200 need only be displayed at a position (for example, the center of an image) and initial transparencies of initial parameters, which are set in advance. A failure message of the alignment processing is displayed, thus prompting the operator to execute position correction processing via the input device 54.

In this case, when the operator modifies the position and changes parameters of the transparencies α, if he or she moves, enlarges/reduces, and rotates the SLO image 201, the map 200 on the SLO image 201 is simultaneously moved, enlarged/reduced, and rotated. That is, the SLO image 201 and map 200 operate as a single image. However, the transparencies α of the SLO image 201 and map 200 are independently set. The parameters which are changed by the operator via the input device 54 are stored in the external storage device 52, and the next or subsequent display operation is made according to the set parameters.

In this manner, the fundus image display field 82 in the fundus image display section 94 displays the two-dimensional fundus image, the map superimposed on the fundus image, and the like. Note that FIGS. 9A and 9B have explained the case in which the contour line map is superimposed in association with a corresponding position on the fundus image. However, the present invention is not limited to this. That is, a curvature map, layer thickness map, and the like may be displayed.

Figure 2:
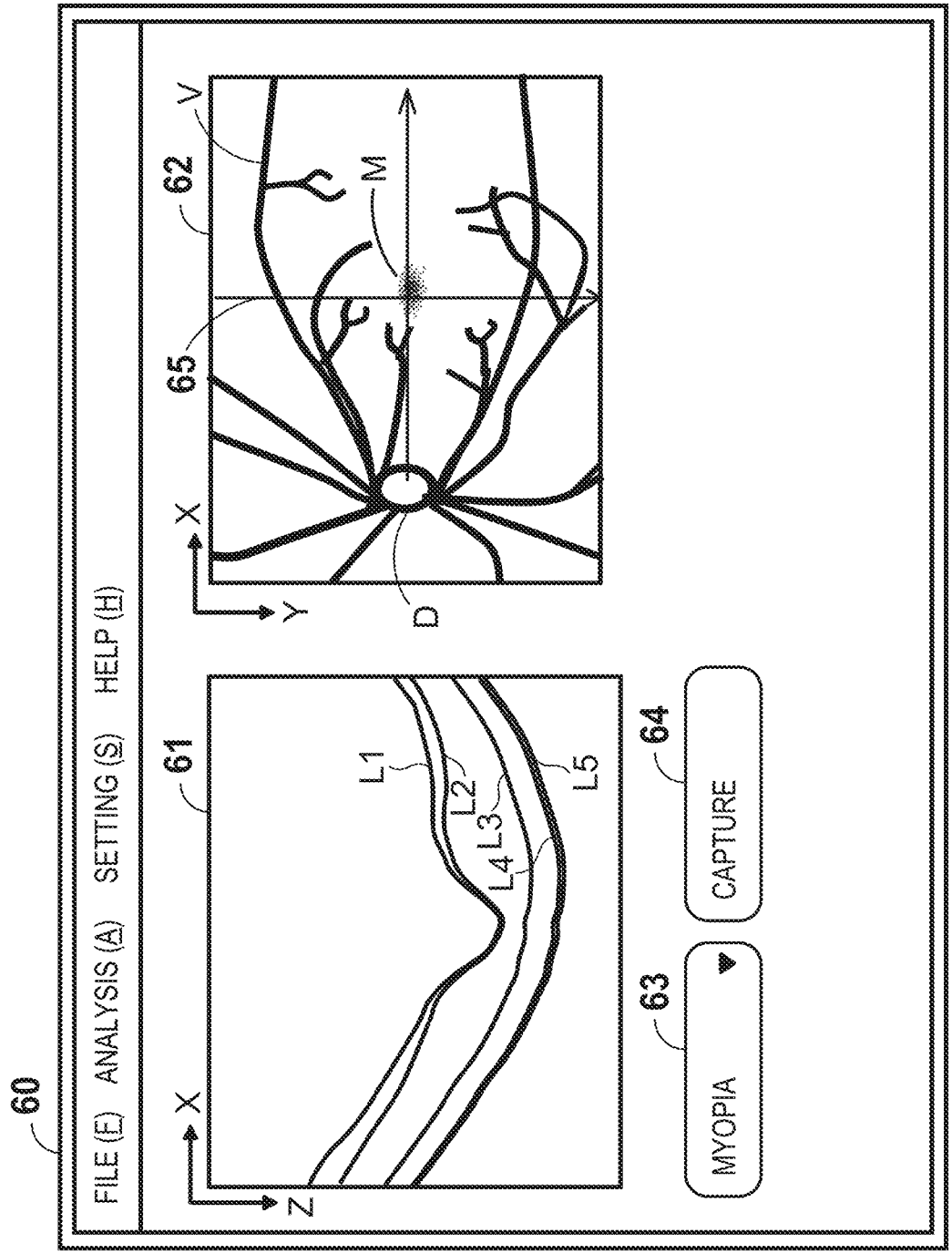
FIG. 2 is a view showing an example of a tomographic image capturing screen 60.

When an analysis target layer is to be changed, the operator can select, for example, the segmentation results (L1 to L5) from the tomographic image on the display field 61 shown in FIG. 2 via the input device 54. When an analysis target layer is switched, the image processing apparatus 30 instructs the display control unit 35 to normally display the segmentation result layer highlighted so far, and to highlight a new analysis target layer. Thus, the analysis results of an arbitrary layer can be displayed.

Details of the first analysis result display section 96 including the first analysis result 84 shown in FIG. 6 will be described below.

The first analysis result 84 displays a shape analysis map generated by the analysis result generation unit 45. A combo box 97 allows the operator to select a map type of the first analysis result 84. In this case, the shape analysis map indicated by the first analysis result 84 is a contour line map.

The type of the shape analysis map indicated as the first analysis result 84 and that of the shape analysis map superimposed on the fundus image described using FIGS.

9A and 9B can be changed in synchronism with each other by designating the type from the combo box 97. Furthermore, the displayed contents on the second analysis result display section 98 to be described later are also changed in synchronism with such designation.

An example of the tomographic image observation screen 80 when the curvature result is displayed as the analysis result will be described below with reference to FIG. 10.

Figure 10:
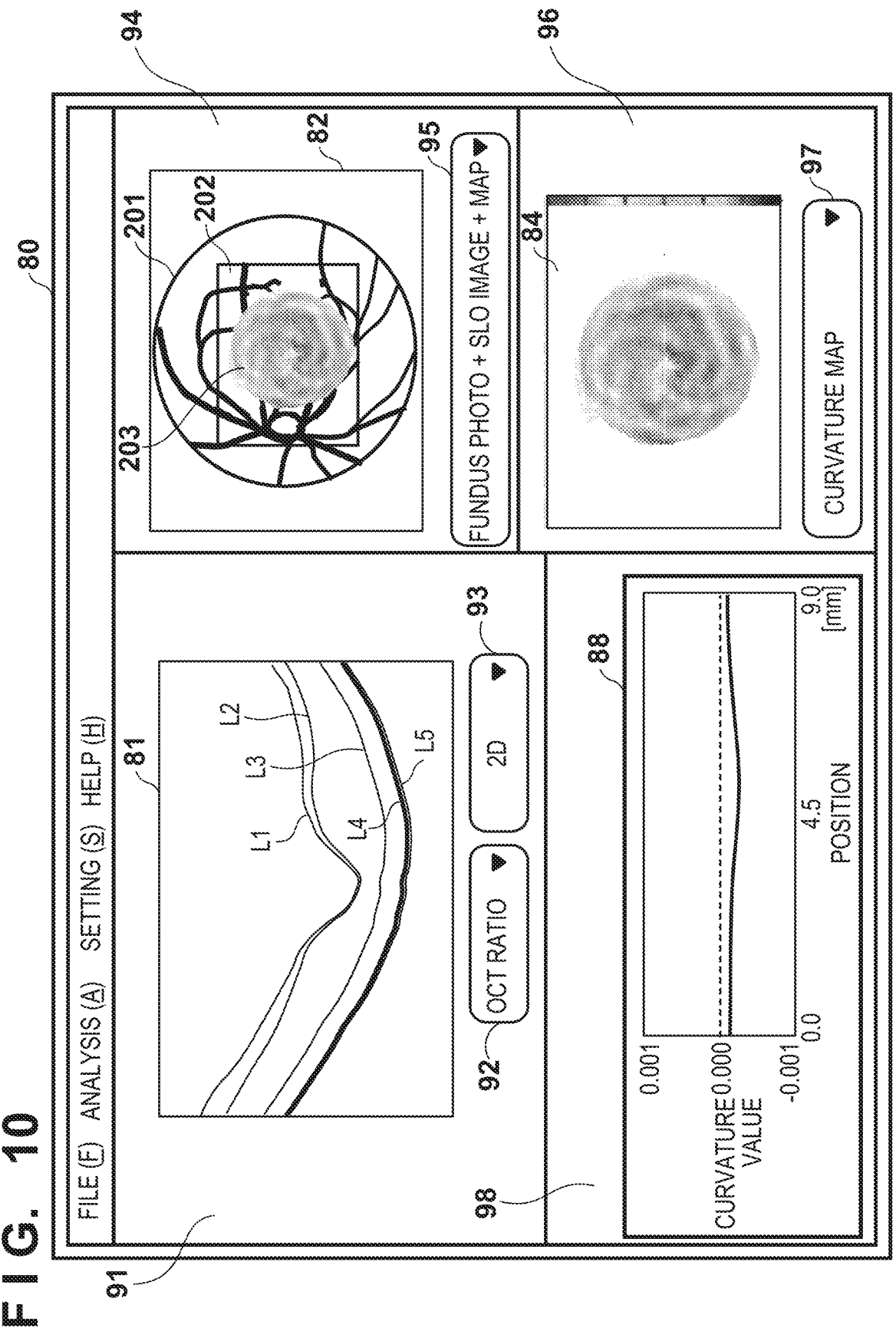
FIG. 10 is a view showing an example of the tomographic image observation screen 80.

When the analysis result to be displayed is switched from that of the area and volume to the curvature analysis result, results displayed on the tomographic image display section 91, fundus image display section 94, first analysis result display section 96, and second analysis result display section 98 have contents shown in FIG. 10.

More specifically, on the tomographic image display field 81, the segmentation results (L1 to L5) of the respective detected layers of the retinal layers are superimposed on a captured tomographic image. A curvature map is displayed as the first analysis result 84, and a curvature graph is displayed as the second analysis result 88. On the fundus image display field 82, an image obtained by superimposing the SLO image (first fundus image) 201, the fundus photo (second fundus image) 202, and a curvature map 203 is displayed.

Details of the second analysis result display section 98 including the second analysis results 85 and 86 shown in FIG. 6 will be described below.

As the second analysis result 85, a shape analysis graph generated by the analysis result generation unit 45 is displayed. In this case, a graph obtained by measuring the area and volume is displayed. The abscissa plots the height (depth), and the ordinate plots the volume. A solid curve 87 represents the volume.

As the second analysis result 86, a shape analysis result is displayed as a table. The table displays an area and volume at a height (for example, 100 µm, 500 µm, or the like) of a given reference value, and an area and volume corresponding to a height (a position of the Bruch's membrane opening) when a certain portion is used as a reference.

Figure 11:
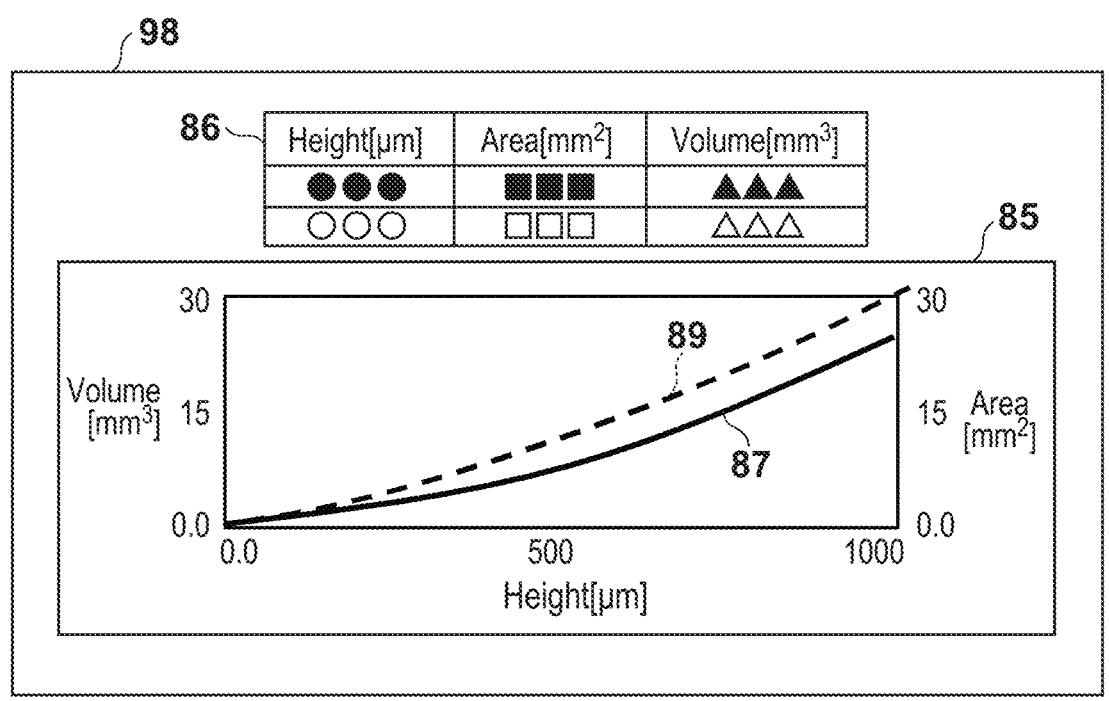
FIG. 11 is a view showing an example of respective components of the tomographic image observation screen 80.

A case will be described below with reference to FIG. 11 wherein area and volume results are displayed on one graph (second analysis result 85). In this case, the abscissa plots the height (depth), the ordinate on the left side of the graph plots the volume, and that on the right side of the graph plots the area. A broken curve 89 is a graph indicating the area, and the solid curve 87 is a graph indicating the volume.

[Step S207]

The image processing apparatus 30 instructs the analysis unit 42 to execute shape analysis based on the detection result of the retinal layer. In this analysis processing, analysis using the detection result of the retinal layer is executed without generating three-dimensional shape data, and the like. For example, the analysis of a layer thickness or the like is executed.

[Step S208]

The image processing apparatus 30 instructs the analysis result generation unit 45 to generate analysis results (for example, a map, graph, and numerical value information) based on the analysis result.

[Step S209]

The image processing apparatus 30 displays a tomographic image, the detection results of layers (RPE, ILM, and the like) detected by the detection unit 41, and analysis results (map, graph, and numerical value information) generated by the analysis result generation unit 45 on the display device 53.

Figure 12:
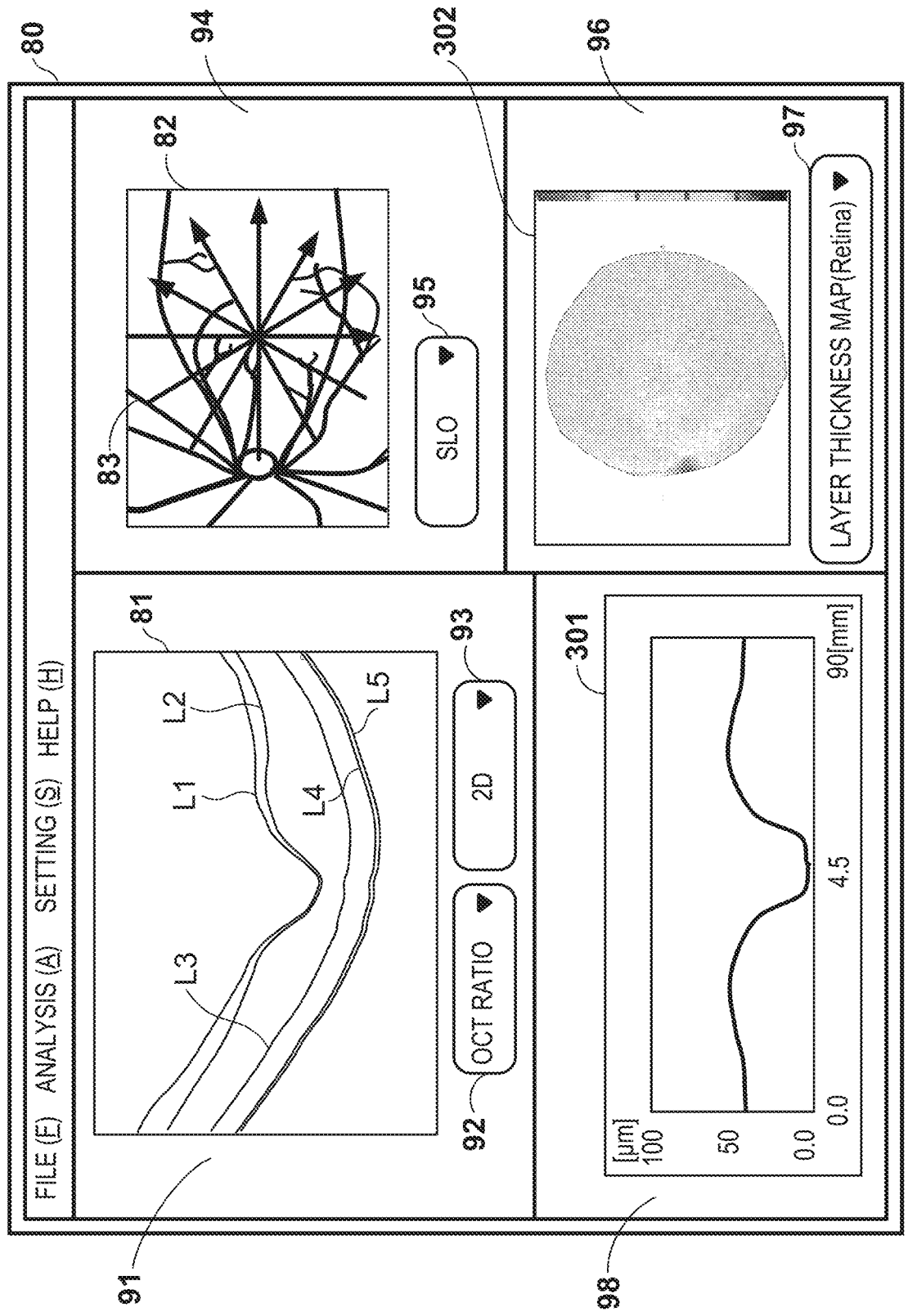
FIG. 12 is a view showing an example of the tomographic image observation screen 80.

FIG. 12 shows an example of the tomographic image observation screen 80 displayed on the display device 53 by the process of step S209.

In this case, a layer thickness map is displayed as a first analysis result 302, and a layer thickness graph is displayed as a second analysis result 301. That is, the analysis results using the detection result of the retinal layer are displayed as the first and second analysis results 302 and 301.

In this case as well, as in the process of step S206, parameters changed by the operator via the input device 54 are stored in the external storage device 52, and the next or subsequent display operation is made according to the set parameters.

As described above, according to the first embodiment, a plurality of imaging modes including that for myopia analysis are provided, and the analysis processing can be selectively executed according to the imaging mode set when a tomographic image is captured.

More specifically, as the plurality of imaging modes, at least the imaging mode for myopia analysis and that for non-myopia analysis are provided. In the imaging mode for myopia analysis, a tomographic image suited to three-dimensional shape analysis (analysis of a macular region in a myopia) is captured.

For a tomographic image captured in the imaging mode for myopia analysis, three-dimensional shape data is generated, and three-dimensional shape analysis is executed based on the shape data. For a tomographic image captured in the imaging mode other than that for myopia analysis, three-dimensional shape data is not generated, and analysis processing based on the detection result of a retinal layer is executed.

Second Embodiment

The second embodiment will be described below. The second embodiment will explain a case in which a tomographic image is displayed simultaneously in 2D and 3D display modes. More specifically, the second embodiment will explain a case in which a tomographic image, three-dimensional shape data, and analysis results are displayed side by side. Note that the second embodiment will exemplify, as a tomographic image, that captured in a radial scan.

Figure 13:
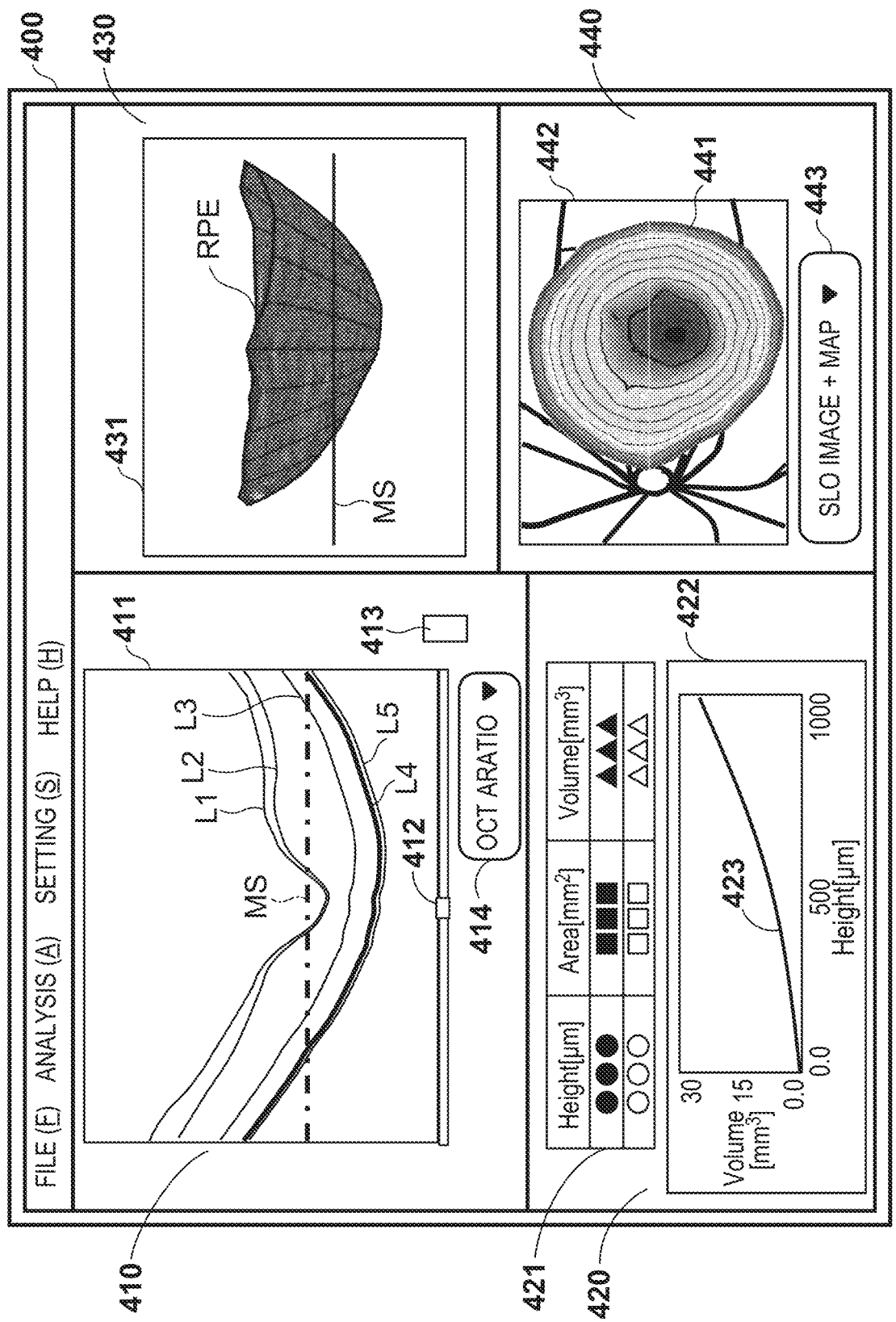
FIG. 13 is a view showing an example of a tomographic image observation screen 400.

An example of a tomographic image observation screen 400 according to the second embodiment will be described below with reference to FIG. 13.

The tomographic image observation screen 400 includes a first tomographic image display section 410 including a two-dimensional tomographic image display field 411, and a second tomographic image display section 430 including a three-dimensional tomographic image display field 431. Furthermore, the tomographic image observation screen 400 includes a first analysis result display section 440 including a first analysis result 442, and a second analysis result display section 420 including second analysis results 421 and 422.

In this embodiment, since the first analysis result display section 440 and second analysis result display section 420 are the same as those shown in FIGS. 6 and 9A used to explain the aforementioned first embodiment, a description thereof will not be repeated. Also, since the second tomographic image display section 430 is the same as that shown in FIGS. 7A to 7C used to explain the first embodiment, a description thereof will not be repeated. In this embodiment, the first tomographic image display section 410 will be mainly described.

The first tomographic image display section 410 includes a slider bar 412 used to change a viewpoint position (slice position) of a tomographic image, and an area 413 used to display a slice number of a tomographic image in addition to the two-dimensional tomographic image display field 411.

Figure 14:
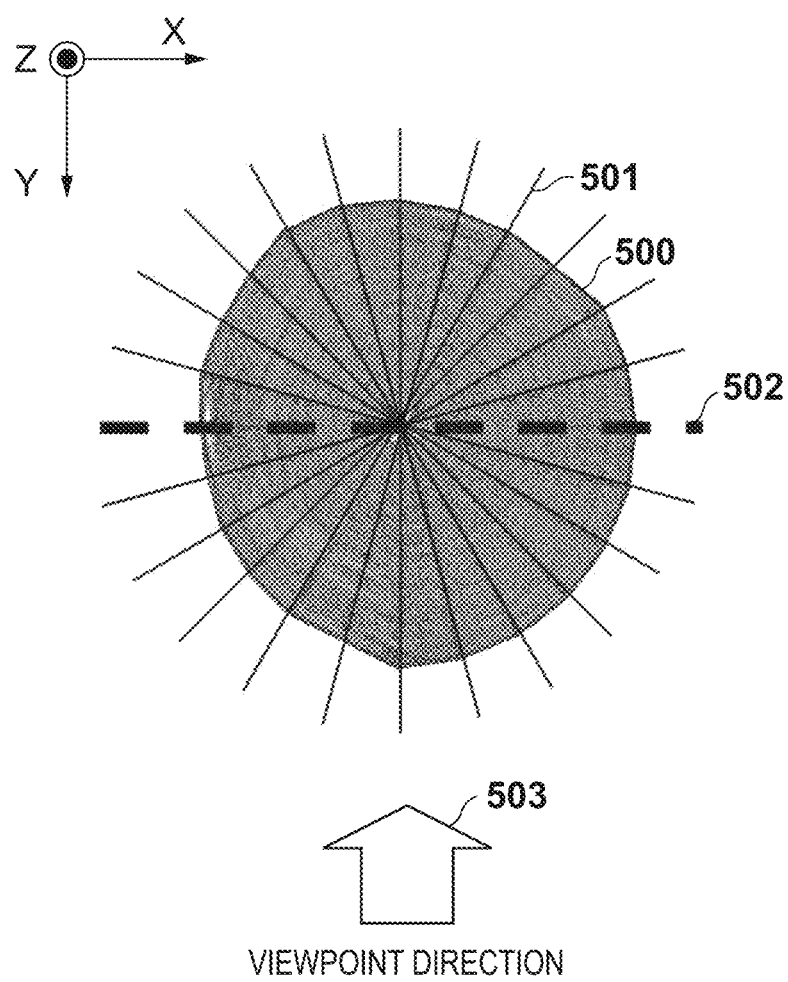
FIG. 14 is a view showing an example of respective components of the tomographic image observation screen 400.

The relationship between a viewpoint direction 503 in a three-dimensional shape and the tomographic image (display field 411) shown in FIG. 13 will be described below with reference to FIG. 14. Reference numeral 500 denotes an overview of a fundus when the three-dimensional shape of the tomographic image is viewed from the above in a depth direction (Z direction). Radial lines 501 indicate imaging slice positions of tomographic images. A broken line 502 indicates a slice position corresponding to the currently displayed tomographic image (display field 411) of the imaging slice positions 501, and this slice position is orthogonal to the viewpoint direction 503. More specifically, the tomographic image at the position 502 is that displayed on the tomographic image display field 411.

A case will be described below wherein the operator operates the tomographic image observation screen 400 described using FIG. 13 via an input device 54.

Assume that the operator moves the position of the slider bar 412 from the center to one end via the input device 54. Then, in synchronism with that operation, an image processing apparatus 30 changes the viewpoint position of the three-dimensional tomographic image (three-dimensional shape data) currently displayed on the display field 431. Also, the image processing apparatus 30 changes the slice position of the two-dimensional tomographic image currently displayed on the display field 411 to a viewpoint position corresponding to a tomographic image designated by the slider bar 412.

Note that when the operator operates the slider bar 412, the position of that bar is continuously changed in place of being discretely changed. For this reason, the position of the three-dimensional shape data of the currently displayed tomographic image is also continuously changed. More specifically, the image processing apparatus 30 displays so that the three-dimensional shape data of the currently displayed tomographic image is rotated with reference to the center in the vertical direction.

Figure 15:
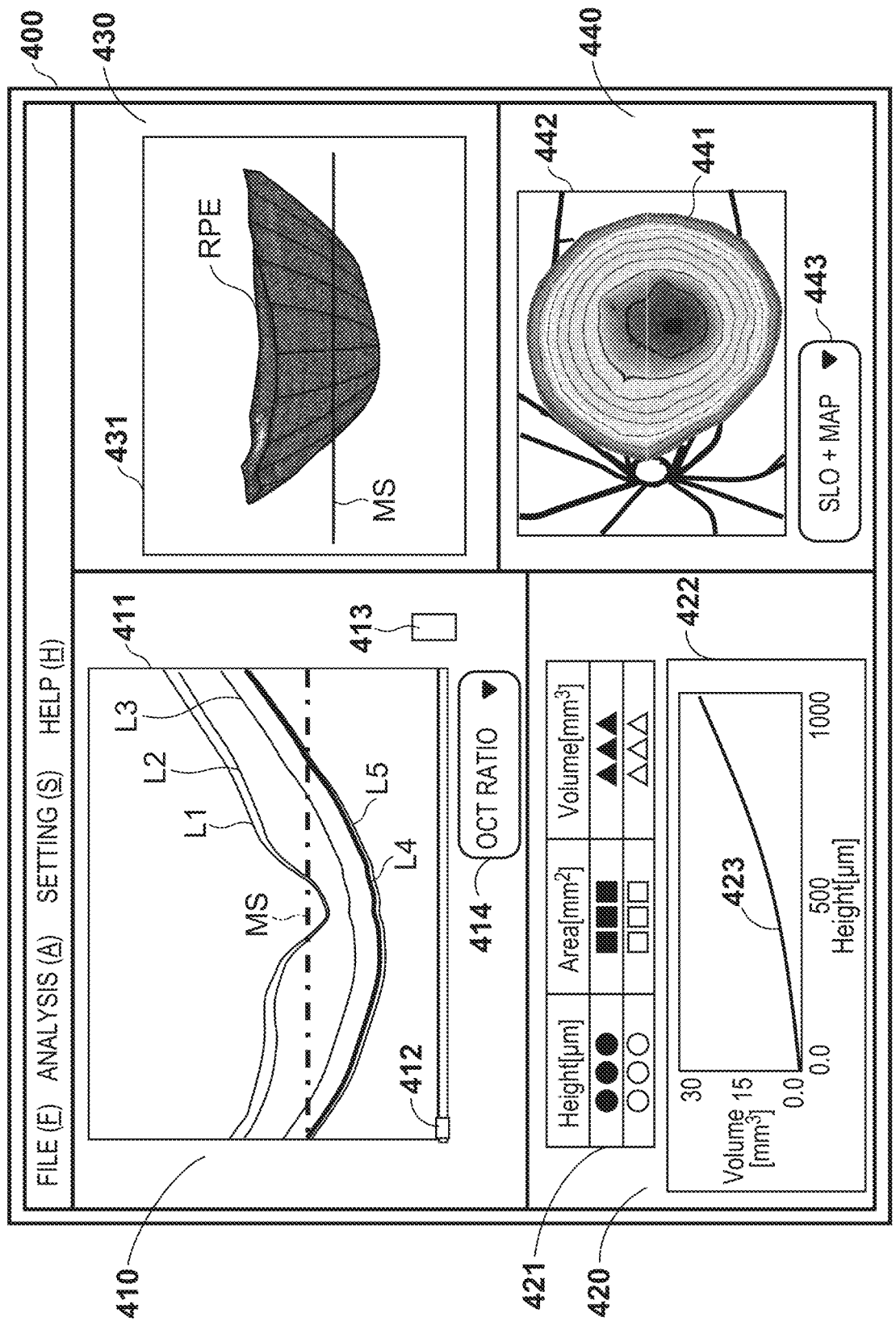
FIG. 15 is a view showing an example of the tomographic image observation screen 400.
Figure 16:
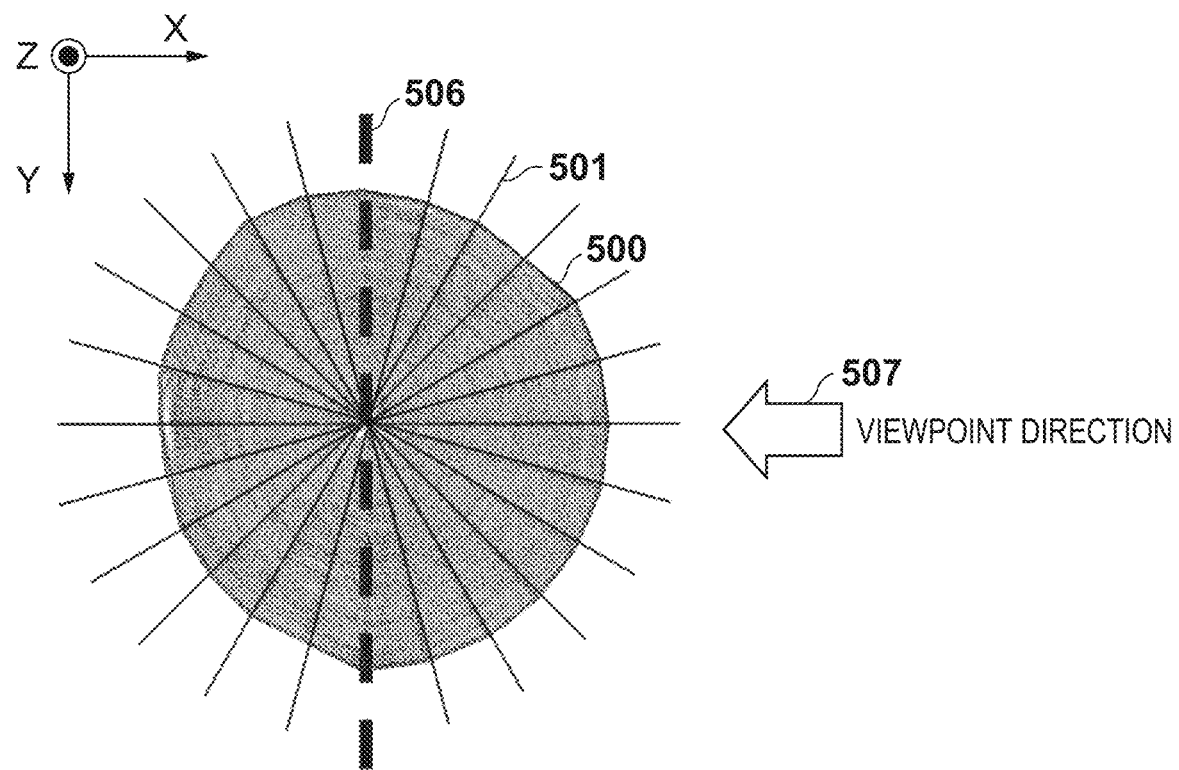
FIG. 16 is a view showing an example of respective components of the tomographic image observation screen 400.

FIG. 15 shows an example of a screen display of the two-dimensional tomographic image on the display field 411 and the three-dimensional tomographic image (three-dimensional shape data) on the display field 431 when the position of the slider bar 412 is moved to one end. In this case, the relationship between a viewpoint direction 507 in the three-dimensional shape and the two-dimensional tomographic image (display field 411) becomes that shown in FIG. 16.

When the position of the slider bar 412 is operated, the image processing apparatus 30 changes the slice position of the two-dimensional tomographic image currently displayed on the display field 411, and also changes the viewpoint position of the three-dimensional tomographic image (three-dimensional shape data) corresponding to that slice position. Note that the viewpoint position of the three-dimensional shape data can be changed according to the operation of the slider bar 412 used to change the slice position of the two-dimensional tomographic image, and vice versa. That is, when the operator changes the viewpoint position of the three-dimensional shape data via the input device 54, the slice position of the two-dimensional tomographic image and the position of the slider bar 412 may be changed accordingly.

As described above, according to the second embodiment, the two-dimensional tomographic image and three-dimensional tomographic image are simultaneously displayed, and their display modes can be changed in synchronism with each other in response to an operation by the operator.

Third Embodiment

The third embodiment will be described below. The third embodiment will explain a case in which both the analysis result of shapes of retinal layers and a statistics database held in a database are comparably displayed.

Figure 17:
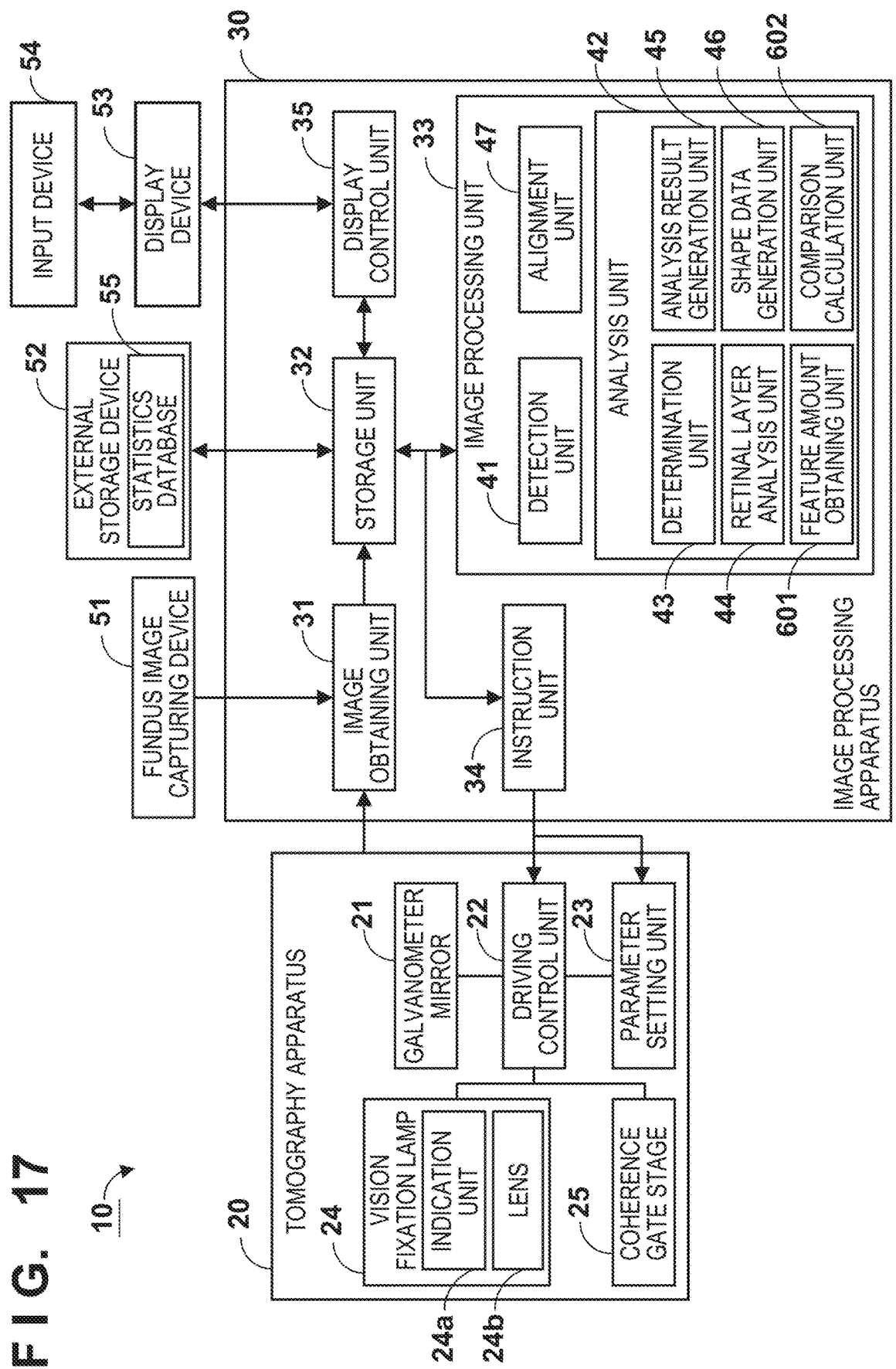
FIG. 17 is a block diagram showing an example of the arrangement of an image processing system 10 according to the third embodiment.

FIG. 17 shows an example of the arrangement of an image processing system 10 according to the third embodiment. In this embodiment, differences from the arrangement shown in FIG. 1 used to explain the first embodiment will be mainly described.

An image processing unit 33 of an image processing apparatus 30 according to the third embodiment newly includes a feature amount obtaining unit 601 and comparison calculation unit 602 in addition to the arrangement of the first embodiment.

The feature amount obtaining unit 601 calculates feature amounts (shape feature amounts) indicating shape features of retinal layers based on three-dimensional shape analysis.

The comparison calculation unit 602 compares shape feature amounts (first feature amounts) with those held in a statistics database 55 stored in an external storage device 52, and outputs the comparison result. Note that the statistics database 55 is generated based on a large number of eye data by integrating race-dependent and age-dependent data. That is, the statistics database 55 holds statistical feature amounts obtained from a plurality of eyes to be examined. Note that in the ophthalmic field, data in the database may be classified based on parameters unique to eyes such as right/left eye-dependent parameters and ophthalmic axis length-dependent parameters.

Figure 18:
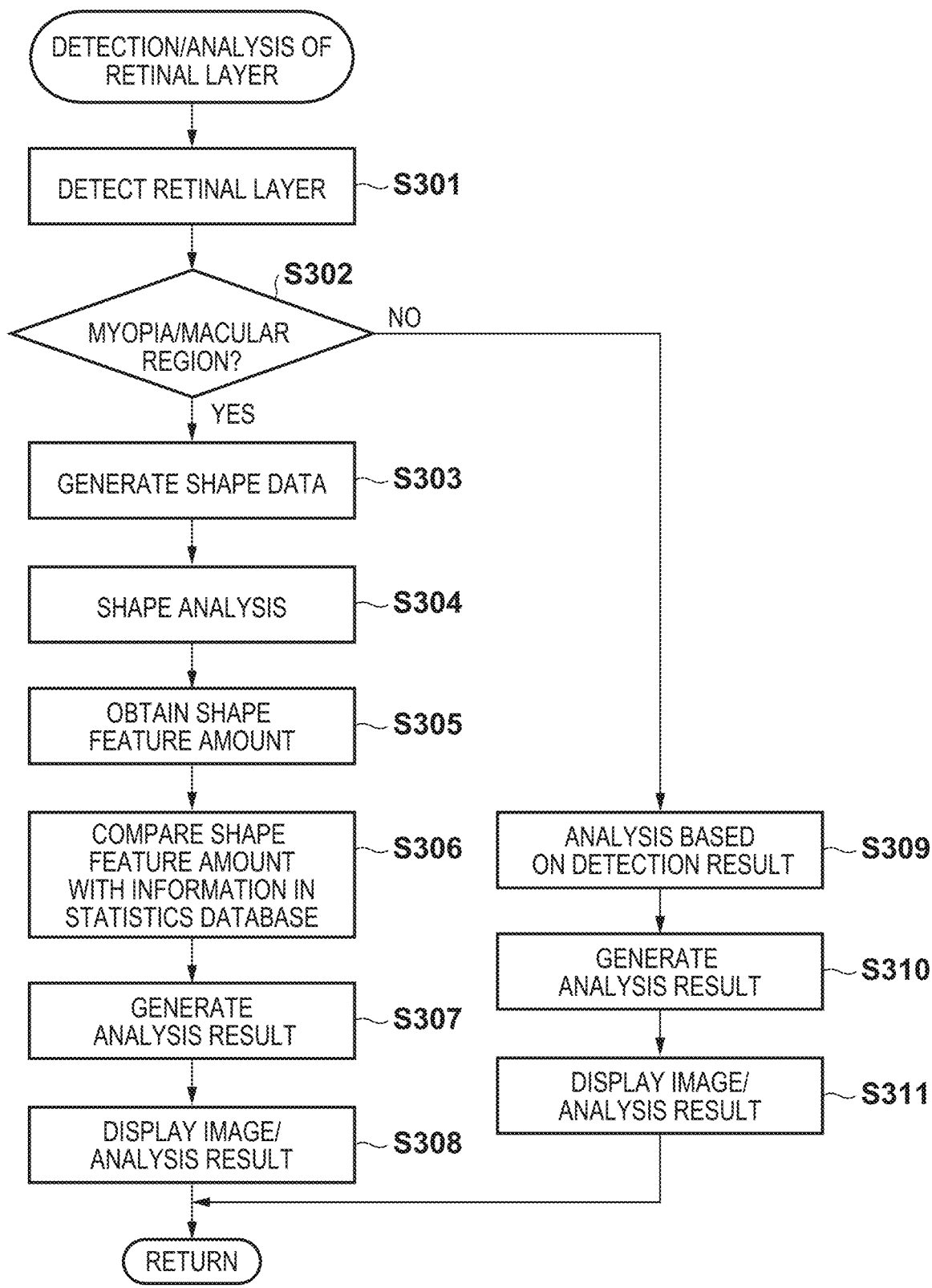
FIG. 18 is a flowchart showing an example of the sequence of processing of an image processing apparatus 30 according to the third embodiment.

An example of the sequence of processing of the image processing apparatus 30 according to the third embodiment will be described below with reference to FIG. 18. Note that the overall processing upon capturing a tomographic image is the same as the contents described using FIG. 3A of the first embodiment, and a description thereof will not be given. Differences from the processing (detection/analysis processing of retinal layers) shown in FIG. 3B will be mainly explained.

[Steps S301 to S304]

Figure 3B:
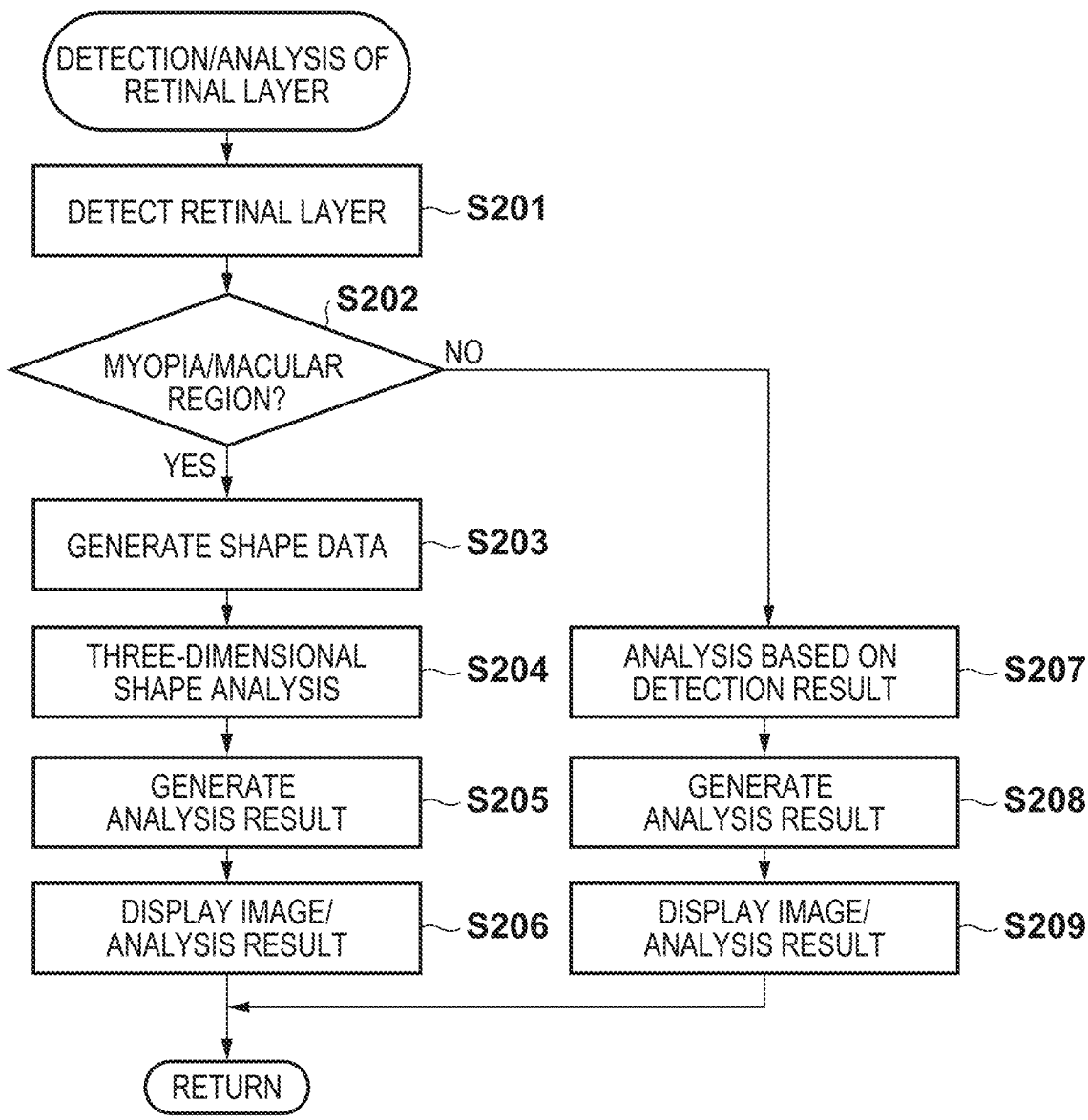

When the detection/analysis processing of retinal layers is started, the image processing apparatus 30 executes the processes of steps S201 to S204 shown in FIG. 3B used to explain the first embodiment. Thus, retinal layers are detected from a tomographic image, and three-dimensional shape analysis of the detected retinal layer is executed.

[Step S305]

The image processing apparatus 30 instructs the feature amount obtaining unit 601 to calculate shape feature amounts based on the three-dimensional shape analysis executed in the process of step S304.

In this case, shape features of the retinal layer include, for example, feature amounts of an area and volume of the retinal layer, a feature amount indicating a degree (of irregularity) of circularity of the retinal layer, a feature amount of a curvature of the shape of the retinal layer, and the like.

The method of calculating the feature amounts of the area and volume of the retinal layer will be described first. The feature amounts of the area and volume of the retinal layer can be obtained by calculating increasing/decreasing rates (typically, increasing rates) of the area and volume of the retinal layer. The area and volume of the retinal layer can be calculated by the same method as in the aforementioned first embodiment.

Upon calculating the increasing/decreasing rates of the area and volume, the feature amount obtaining unit 601 respectively calculates areas and volumes at given heights (depths) such as 100 μm, 200μ, and 300 μm from the deepest portion of the RPE based on the analysis result of the three-dimensional shape analysis by an analysis unit 42. Then, based on the results, the increasing/decreasing rates of the area and volume are calculated as shape features of the retinal layer.

The feature amount indicating the degree (of irregularity) of circularity of the retinal layer is calculated from, for example, the sectional shape of the retinal layer to be (finally) used as an area measurement target. The calculation method of the feature amount indicating the degree (of irregularity) of circularity of the retinal layer will be described below with reference to FIGS. 19A and 19B while taking a practical example.

Figure 19A:
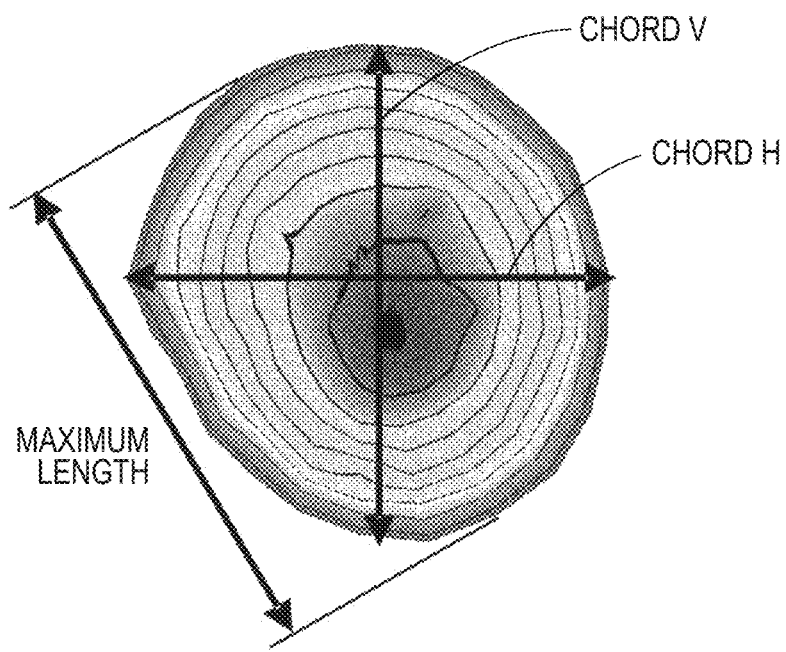
FIGS. 19A and 19B are views showing an overview of a method of obtaining feature amounts which represent shape features of retinal layers.
Figure 19B:
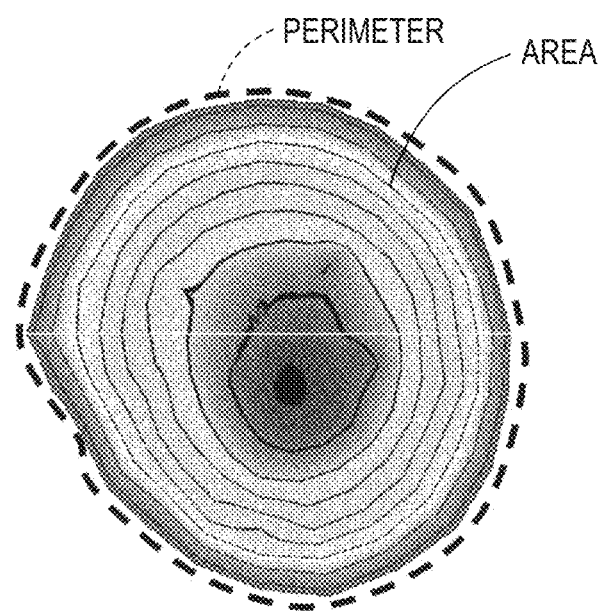

FIG. 19A shows a horizontal maximum chord length (CHORD H), vertical maximum chord length (CHORD V), and absolute maximum length (MAXIMUM LENGTH). FIG. 19B shows an area (AREA) and perimeter (PERIMETER). A degree $C_L$ of circularity can be calculated from these values. An equation of the degree of circularity is described as:

$$C_L = \frac{4\pi A}{L^2} \quad (2)$$

where A is an area (AREA), and L is a perimeter (PERIMETER). By calculating a reciprocal of the degree of circularity, a feature amount indicating a degree of irregularity can be obtained. Of course, the method of calculating the feature amount indicating the degree of irregularity of circularity is not limited to this, and for example, a moment feature around the barycenter may be used.

Subsequently, the method of calculating the feature amount of the curvature of the shape of the retinal layer will be described below. Upon calculating the feature amount of the curvature, the feature amount obtaining unit 601 calculates curvatures at respective portions of the retinal layer, and calculates an average, variance, and standard deviation of the curvatures at all the positions.

When the curvature value is calculated as a signed curvature value in place of an absolute value, the irregularity of the shape can be recognized based on positive/negative values. For this reason, upon calculating the signed curvature values, the number of positive curvature values and that of negative curvature values are respectively counted as a curvature value. In counts of the numbers of positive and negative curvature values, a curvature value of a perfect line becomes zero. However, upon automatic or manual detection of the retinal layer, some errors are included. For this reason, values around the curvature value=0 may be excluded from the counts, and only large positive and negative curvature values, that is, only positions with large features may be counted.

[Step S306]

The image processing apparatus 30 instructs the comparison calculation unit 602 to compare the feature amounts obtained by the process of step S305 and those in the statistics database 55 stored in the external storage device 52. Note that the statistics database 55 holds information in which a 95% range of normal data is a normal range, a 4% range is border line range, and the remaining 1% range is an abnormal range.

The comparison calculation unit 602 compares in which of ranges the analysis results and feature amount values calculated by the processes of steps S304 and S305 are located with respect to feature amounts held in the statistics database 55. For example, only the area and volume of the analysis results may be compared, or the values of the area and volume and feature amount values are plotted on two axes, and comparison may be made to decide their locations. Furthermore, when the feature amount is a curvature, the average value and variance value of the curvature values are plotted on two axes, and comparison may be made to decide their ranges.

Figure 20A:
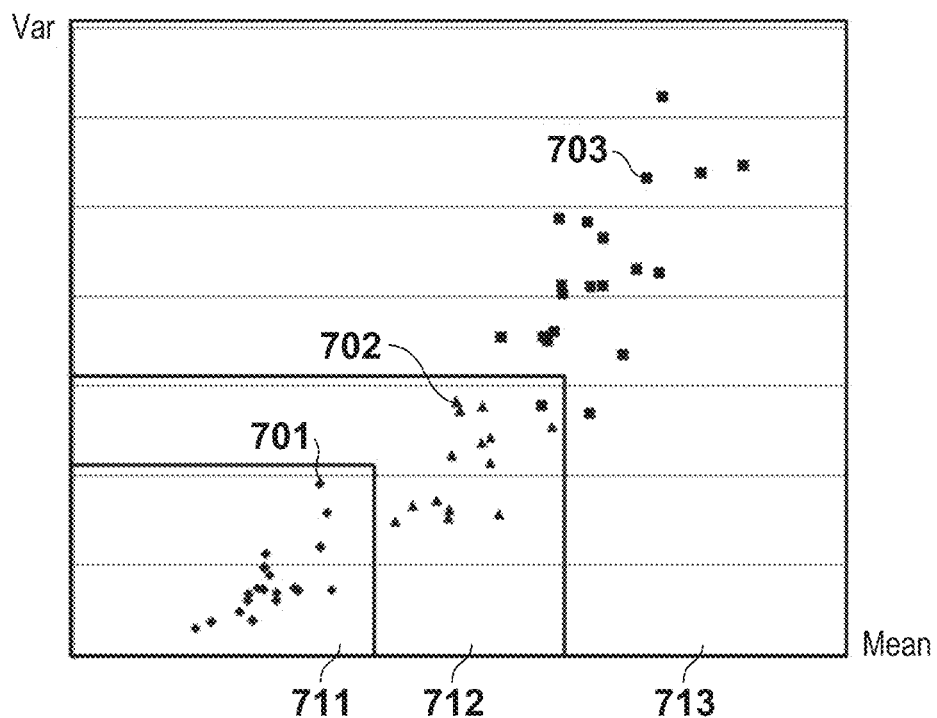
FIGS. 20A and 20B are views showing an overview of a method of obtaining feature amounts which represent shape features of retinal layers.

This point will be further explained. In a graph shown in FIG. 20A, the abscissa plots the average value of curvatures, and the ordinate plots the variance value of curvatures. A rhombus 701 indicates a curvature value of a retinal layer free from any symptom of posterior staphyloma in a myopia, and a triangle 702 indicates a curvature value of a retinal layer which suffers a mild symptom of posterior staphyloma in a myopia. Also, a rectangle 703 indicates a curvature value of a retinal layer which suffers a symptom of posterior staphyloma in a myopia.

Note that posterior staphyloma means a state of an eyeball, the shape of which is deformed to be projected backward. A plurality of plot points indicate the number of cases, and this graph indicates plots of several ten cases. In this case, a description of the shape feature amounts obtained by the process of step S305 will not be given, and these shape feature amounts are plotted on the graph in a format (for example, a display format (for example, circle) is changed) identifiable from feature amounts held in the statistics database 55. That is, the shape feature amounts obtained by the process of step S305 are displayed to be comparable with feature amounts held in the statistics database 55.

In this case, a region 711 indicates a curvature value region free from a symptom of posterior staphyloma, a region 712 indicates a curvature range region suffering a mild symptom of posterior staphyloma, and a region 713 indicates a curvature value region suffering a symptom of posterior staphyloma. Therefore, for example, when a curvature value of an eye to be examined as a target is measured, if the curvature value of that eye to be examined is located in the region 711, it is determined that the eye is free from posterior staphyloma; if the curvature value is located in the region 713, it is determined that the eye suffers posterior staphyloma.

As described above, according to this embodiment, the graph is classified into a plurality of regions which indicate possibility levels indicating if an eye to be examined suffers a disease stepwise (that is, a display mode indicating stepwise categories of symptoms of a disease of an eyes to be examined), and curvature values (feature amounts) are plotted on the graph to be displayed. Also, depending on a region to which a curvature value belongs, a display format (rhombus, triangle, or rectangle) of an object indicating a curvature value is changed and displayed. Note that the graph is classified into three regions for the sake of simplicity, but the present invention is not limited to this. For example, each of the regions may be divided into a plurality of sub-regions to be classified into a total of 10 levels, so as to allow the operator to determine a degree of posterior staphyloma.

[Step S307]

The image processing apparatus 30 instructs an analysis result generation unit 45 to generate an analysis result based on the result of the process of step S305. The analysis result is generated in a format which allows the operator to recognize a location of analysis values of an eye to be examined as a target in the statistics database 55.

Figure 20B:

As an example of the analysis result, for example, as described above using FIG. 20A, when the statistics database 55 is expressed by two dimensions, a graph on which curvature values of the eye to be examined are plotted to indicate their regions may be used. Alternatively, as shown in FIG. 20B, a color bar (bar graph) which expresses features of the statistics database 55 by one dimension may be generated, and an analysis result indicating a position on that color bar (bar graph) may be generated.

Furthermore, when one value corresponds to each position like curvature values, it may be compared with an arbitrary curvature value held in the statistics database 55 at that position to generate a two-dimensional map which allows to recognize locations in the statistics database 55. Note that in the two-dimensional map, an average value of those within a given range may be compared to the statistics database 55 in place of comparison at each position.

[Step S308]

The image processing apparatus 30 instructs a display control unit 35 to display a tomographic image, the detection result of the layers detected by a detection unit 41, and analysis results (map, graph, and numerical value information) generated by the analysis result generation unit 45 on a display device 53. Note that as the analysis results, the map, graph, and the like generated by the process of step S307 may be displayed. More specifically, a tomographic image observation screen 80 shown in FIG. 21 is displayed.

In this case, as a first analysis result 84, a curvature map of the retinal layer is displayed as the comparison results with the feature amounts (curvatures) in the statistics database 55. This curvature map presents the comparison results of average values of given ranges with the statistics database 55. A darker color portion indicates that a curvature value falls outside a normal value range of the statistics database 55, and a lighter color portion indicates that a curvature value falls within the normal value range of the statistics database 55.

A second analysis result display section 98 displays a graph 730 indicating a position of an average value and variance value of curvatures in the statistics database 55. A circular point 722 in the graph 730 is a plot of the analysis value of the eye to be examined as a target in this graph.

In the screen example shown in FIG. 21, only one map and one graph are displayed. However, the present invention is not limited to this. For example, an area/volume map and the curvature map may be displayed side by side in a first analysis result display section 96. At the same time, an area/volume graph and the curvature graph may be displayed side by side in the second analysis result display section 98.

As described above, according to the third embodiment, feature amounts (shape feature amounts: first feature amounts) indicating shape features of a retinal layer and shape feature amounts (second feature amounts) corresponding to a plurality of eyes to be examined which are held in advance in the statistics database can be displayed (presented) for the operator. Thus, the shape feature amounts of an eye to be examined as a diagnosis target can be presented together with an index as a criterion as to whether or not the eye to be examined suffers a disease.

Fourth Embodiment

The fourth embodiment will be described below. The fourth embodiment will explain the following case. That is, feature amounts held in a statistics database are searched for using shape features (shape feature amounts) of a retinal layer and image features (image feature amounts) of a tomographic image or fundus image. Then, a tomographic image, fundus image, and diagnosis information of an eye to be examined having feature amounts close to the shape features of the current eye to be examined are displayed.

Figure 22:
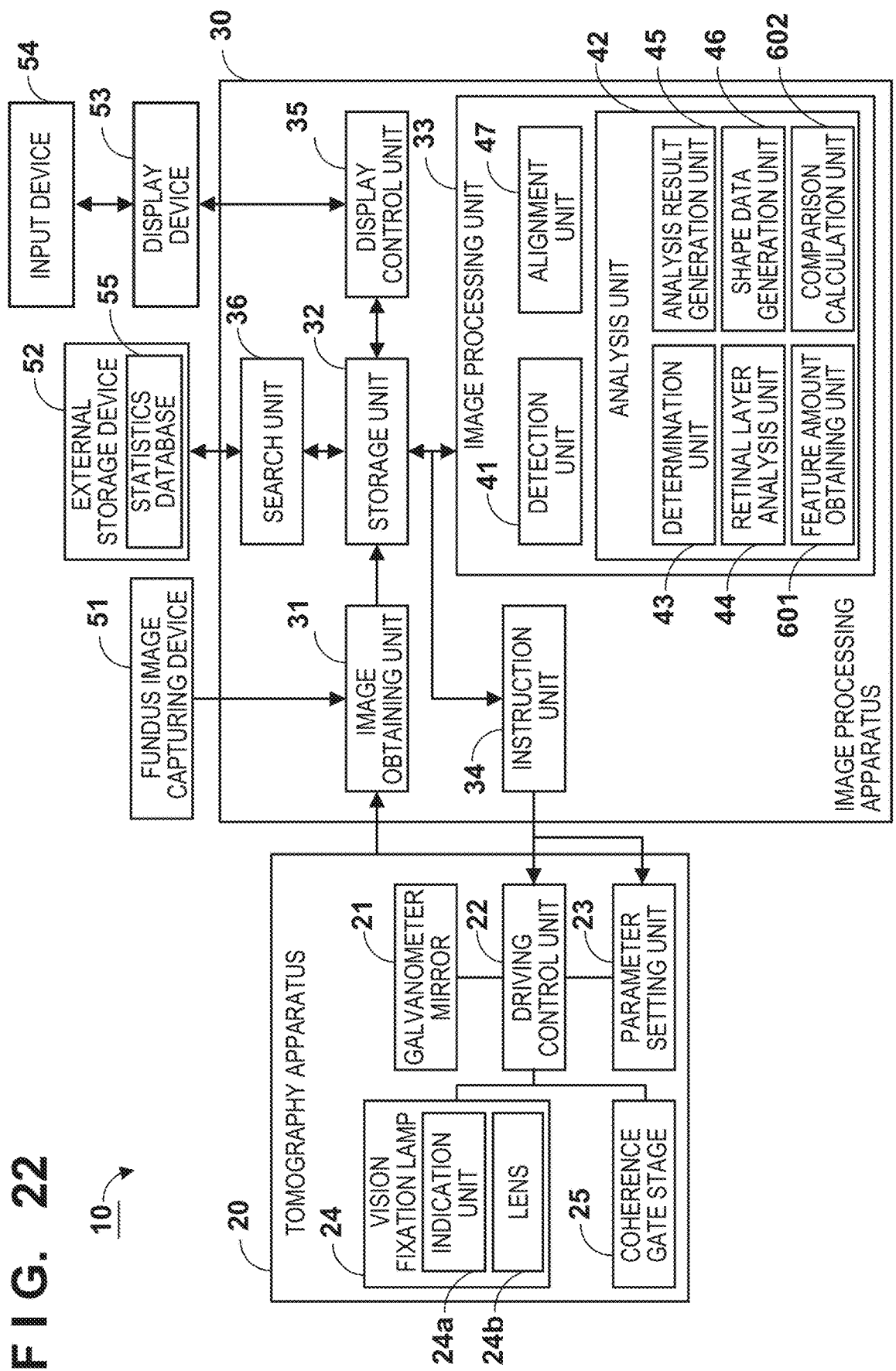
FIG. 22 is a block diagram showing an example of the arrangement of an image processing system 10 according to the fourth embodiment.

FIG. 22 shows an example of the arrangement of an image processing system 10 according to the fourth embodiment. In this embodiment, differences from the arrangement of FIG. 17 used to explain the third embodiment will be mainly described. An image processing apparatus 30 according to the fourth embodiment newly includes a search unit 36 in addition to the arrangement of the third embodiment.

An external storage device 52 according to the fourth embodiment stores feature amounts of retinal layers, tomographic images, fundus images, and diagnosis information in association with each other as a statistics database 55. The search unit 36 searches the external storage device 52 (that is, the statistics database 55) using shape features of a retinal layer and image features in a tomographic image or fundus image.

An example of the sequence of processing of the image processing apparatus 30 according to the fourth embodiment will be described below. Since the processing of the image processing apparatus 30 according to the fourth embodiment is executed in the same sequence as that of the aforementioned third embodiment, different processes will be mainly described below using FIG. 18 described above. The different processes include those of steps S305, S306, and S308.

[Step S305]

The image processing apparatus 30 instructs a feature amount obtaining unit 601 to extract image feature amounts from a tomographic image or fundus image in addition to shape feature amounts described in the aforementioned third embodiment. The image feature amounts include, for example, edge features, color features, histogram features, SIFT (Scale-Invariant Feature Transform) feature amounts, and the like.

[Step S306]

The image processing apparatus 30 instructs the search unit 36 to express the shape feature amounts and image feature amounts obtained by the process of step S305 as a multi-dimensional vector, and to compare these feature amounts with data held in the statistics database 55 in the external storage device 52. Thus, an image having similar feature amounts is searched for. As a search method, a nearest neighbor search may be used. Note that an approximate nearest neighbor search or the like may be used to speed up the processing.

[Step S308]

The image processing apparatus 30 instructs a display control unit 35 to display a screen including a captured tomographic image and a similar tomographic image obtained by the search of a search unit 36 on a display device 53.

More specifically, a tomographic image observation screen 900 shown in FIG. 23 is displayed. The tomographic image observation screen 900 includes a first analysis result display section 930 for displaying current image analysis results, and a second analysis result display section 940 for displaying previous image analysis results.

The first analysis result display section 930 displays a tomographic image 901, SLO image 903, fundus photo 902, (three-dimensional shape) analysis result map 904, and analysis graph 905. A circular point 906 in the analysis graph 905 indicates a plot result of the analysis value of the eye to be examined as a target in the graph. Also, star-like points 907 indicate plot results of the analysis values of previous eyes to be examined displayed on the second analysis result display section 940 in the graph. In this case, in the analysis graph 905, the abscissa plots the shape feature amounts, and the ordinate plots the image feature amounts. Of course, the present invention is not limited to this. As the analysis result, a graph indicating curvature values described in the third embodiment or the like may be displayed.

The second analysis result display section 940 displays tomographic images 911 and 921, SLO images 913 and 923, fundus photos 912 and 922, (three-dimensional shape) analysis result maps 914 and 924, and pieces of diagnosis information 915 and 925 of eyes to be examined. The diagnosis information is information indicating diagnosis processes, and includes, for example, an age, diagnostic name, treatment history, visual acuity, refractometric value, keratometric value, ophthalmic axis length, and the like. In case of FIG. 23, images and diagnosis information of an identical eye to be examined are displayed along a vertical column. Of course, images and diagnosis information of an identical eye to be examined may be displayed side by side along a horizontal row.

When there are a plurality of images similar to the current eye to be examined, the operator operates a slider bar 950 via an input device 54 to selectively display these results. Note that previous similar images to be displayed may be switched using a member other than a slider bar 950. For example, when the operator clicks a star-like point 907 on the analysis graph 905 via the input device (for example, a mouse) 54, an image having that feature amount may be displayed beside the current image.

As described above, according to the fourth embodiment, the statistics database is searched for tomographic images similar to a captured tomographic image of an eye to be examined and associated information based on feature amounts (shape feature amounts) indicating shape features of a retinal layer and image feature amounts of a tomographic image or fundus image. Then, the similar tomographic images and associated information are displayed side by side together with the captured tomographic image. Thus, the shape feature amounts of an eye to be examined as a diagnosis target can be presented together with an index used as a criterion as to whether or not the eye to be examined suffers a disease.

The representative embodiments of the present invention have been described. However, the present invention is not limited to the above and illustrated embodiments, and the present invention can be practiced while being modified as needed without departing from its scope.

For example, on some screens described in the aforementioned first to fourth embodiments, check boxes, combo boxes, and the like are arranged. Radio buttons, list boxes, buttons, and the like may be changed as needed as usage. For example, components described as the combo boxes in the aforementioned description may be implemented as list boxes.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing system comprising:
a memory that stores a program; and
a processor that executes the program stored in the memory so as to function as units including:
an image obtaining unit configured to obtain a fundus image captured by a fundus imaging device and a plurality of tomographic images captured by a tomographic imaging apparatus;
a detection unit configured to detect a retinal layer of a fundus retina in each of the plurality of tomographic images;
a feature amount obtaining unit configured to obtain a feature amount of the retinal layer of the fundus retina based on the detected retinal layer of the each of the plurality of tomographic images;
a map generation unit configured to generate a feature amount map based on the feature amount of the retinal layer; and
a display control unit configured to display side by side a current image analysis result of a current plurality of tomographic images and a previous image analysis result of a previous plurality of tomographic images on a display screen, each of the current image analysis result including the current tomographic image, a current fundus image and a current feature amount map superimposed on the current fundus image and the previous image analysis result including the previous tomographic image, a previous fundus image and a previous feature amount map superimposed on the previous fundus image.

2. The image processing system according to claim 1, wherein the feature amount map is at least one of a thickness map indicating thicknesses and a curvature map indicating curvatures calculated at respective parts on the detected retinal layer in the tomographic image.

3. The image processing system according to claim 1, wherein the units further include a selecting unit configured to select a retinal layer for an analysis target layer, and
an analysis unit configured to obtain, as the current image analysis result, a shape analysis information with reference to the feature amount of the retinal layer selected by the selecting unit.

4. The image processing system according to claim 1, further comprising a plurality of imaging modes including an imaging mode for myopia analysis,
wherein the feature amount obtaining unit obtains the feature amount of the plurality of tomographic images in a case where the imaging mode is the imaging mode for myopia analysis when the plurality of tomographic images are captured.

5. The image processing system according to claim 1, further comprising a database configured to hold the tomographic images and a plurality of feature amounts of retinal layers,
wherein the units further include a search unit configured to search the database for the tomographic images so as to obtain the previous image analysis result.

6. The image processing system according to claim 1, wherein the units further include an alignment unit configured to align the fundus image and the feature amount map, and
wherein the display control unit is configured to display the feature amount map superimposed on the fundus image based on a result of alignment by the alignment unit.

7. The image processing system according to claim 1, further comprising a SLO (Scanning Laser Ophthalmoscope), wherein the fundus image is an SLO image captured by the SLO.

8. The image processing system according to claim 1, wherein the display control unit further displays an analysis graph indicating the current image analysis result of an eye to be examined.

9. The image processing system according to claim 1, wherein the display control unit further displays diagnosis information indicating the previous image analysis result of an eye to be examined.

10. An image processing method comprising:
obtaining a fundus image captured by a fundus imaging device and a plurality of tomographic images captured by an tomographic imaging apparatus;
detecting a retinal layer of a fundus retina in each of the plurality of tomographic images;
obtaining a feature amount of the retinal layer of the fundus retina based on the detected retinal layer of the each of the plurality of tomographic images;
generating a feature amount map based on the feature amount of the retinal layer; and
displaying side by side a current image analysis result of a current plurality of tomographic images and a previous image analysis result of a previous plurality of tomographic images on a display screen, the current image analysis result including the current tomographic image, a current fundus image and a current feature amount map superimposed on the current fundus image and the previous image analysis result including the previous tomographic image, a previous fundus image and a previous feature amount map superimposed on the previous fundus image.

11. The image processing method according to claim 10, wherein the feature amount map is at least one of a thickness map indicating thicknesses and a curvature map indicating curvatures calculated at respective parts on the detected retinal layer in the tomographic image.

12. The image processing method according to claim 10, further comprising searching a database for the tomographic images so as to obtain the previous image analysis result,
wherein the database holds the tomographic images and a plurality of feature amounts of retinal layers.

* * * * *